(12) United States Patent
Masilamani et al.

(10) Patent No.: US 8,208,142 B2
(45) Date of Patent: Jun. 26, 2012

(54) LUNG CANCER DETECTION BY OPTICAL ANALYSIS OF BODY FLUIDS

(75) Inventors: Vadivel Masilamani, Riyadh (SA); Masilamani Elangovan, Fairfax, VA (US); Mohamad Alsalhi, Riyadh (SA); Abdul Rahman Al-Diab, Riyadh (SA)

(73) Assignee: King Salid University, Riyadh (SA)

( * ) Notice: Subject to any disclaimer, the term of this patent is extended or adjusted under 35 U.S.C. 154(b) by 381 days.

(21) Appl. No.: 12/591,749

(22) Filed: Nov. 30, 2009

(65) Prior Publication Data

US 2010/0075367 A1   Mar. 25, 2010

Related U.S. Application Data

(63) Continuation-in-part of application No. 12/458,489, filed on Jul. 14, 2009, now abandoned, which is a continuation-in-part of application No. 12/285,670, filed on Oct. 10, 2008, now Pat. No. 7,869,033, which is a continuation-in-part of application No. 12/000,233, filed on Dec. 11, 2007, now abandoned, which is a continuation-in-part of application No. 11/017,913, filed on Dec. 22, 2004, now abandoned.

(60) Provisional application No. 61/129,728, filed on Jul. 15, 2008, provisional application No. 60/531,987, filed on Dec. 24, 2003.

(51) Int. Cl.
*G01N 21/25* (2006.01)

(52) U.S. Cl. ........................................... 356/417

(58) Field of Classification Search .................. 356/417; 250/459.1
See application file for complete search history.

(56) References Cited

U.S. PATENT DOCUMENTS

| | | | |
|---|---|---|---|
| 4,541,438 A | 9/1985 | Parker et al. | |
| 4,933,274 A | 6/1990 | Sanford et al. | |
| 5,131,398 A | 7/1992 | Alfano et al. | |
| 5,270,171 A | 12/1993 | Cercek et al. | |
| 5,422,093 A | 6/1995 | Kennedy et al. | |
| 5,579,773 A | 12/1996 | Vo-Dinh et al. | |
| 5,864,397 A * | 1/1999 | Vo-Dinh ................... | 356/301 |
| 6,080,584 A | 6/2000 | Alfano et al. | |
| 6,083,487 A | 7/2000 | Biel | |
| 6,091,985 A | 7/2000 | Alfano et al. | |
| 6,256,530 B1 | 7/2001 | Wolfe | |
| 6,316,215 B1 | 11/2001 | Adair et al. | |

(Continued)

OTHER PUBLICATIONS

Natural Fluorescence Spectroscopy of Human Blood Plasma Diagnosis of Colorectal Cancer: Feasibility Study and Preliminary Results. Tumori, vol. 93, No. 6, pp. 567-571, Oct. Nov.-Dec. 2007, Lualdi et al.

(Continued)

*Primary Examiner* — Tarifur Chowdhury
*Assistant Examiner* — Abdullahi Nur
(74) *Attorney, Agent, or Firm* — Richard C. Litman

(57) ABSTRACT

The method for lung cancer detection by optical analysis of body fluids relates to analyzing samples of blood, urine and sputum by fluorescence spectroscopy in order to detect the presence of naturally occurring molecules in the fluids that serve as biomarkers indicative of cancer in the human body. The analysis can be carried out based on fluorescence emission spectra, fluorescence excitation spectra and synchronous (emission and excitation) spectra of bio-samples. The early detection and diagnosis of lung cancer may be made by comparison of ratios of fluorescence emissions and/or excitation intensities of tryptophan, tyrosine, elastin, collagen, bile pigments, NADPH, flavins and various species of porphyrins.

18 Claims, 19 Drawing Sheets

U.S. PATENT DOCUMENTS

| | | |
|---|---|---|
| 6,696,241 B2 | 2/2004 | Thompson et al. |
| 6,750,037 B2 | 6/2004 | Adair et al. |
| 6,984,498 B2 | 1/2006 | Adair |
| 2002/0115121 A1 | 8/2002 | Garwin |
| 2004/0202612 A1 | 10/2004 | Adair |

OTHER PUBLICATIONS

Lasers in Surgery and Medicine, Characteristic Autofluorescence for Cancer Diagnosis and its Origin. Lasers in Surgery and Medicine. vol. 7, No. 6, pp. 528-532, Oct. 19, 2005. Yuanlong et al.

Fluorescence Spectroscopy. A Technique with Potential to Improve the Early Detection of Aerodigestive Tract Neoplasia. Basic Review. pp. 556-562, Aug. 27, 1997. Gillenwater et al.

Detection of Cancer of Pancreas by Native Fluorescence of Blood Components—a Preliminary Report. Emirates Medical Journal vol. 25 No. 1 Jan. 2007. Ibrahim Al-Diab et al.

Spectroscopy of Human Blood Plasma for Cancer Detection: Feasibility Study and Preliminary Results. Gastrointestinal Cancers Symposium Natural Fluorescence Abstract No. 394, 2008. Jan. 25-27, 2008 (abstract). Leo et al.

Research on Fluorescence Spectra of Cancer Blood. Optics in Health Care and Biochemical Optics III, Abstract, Nov. 12, 2007 (abstract). Liu et al.

A correlation of Fluorescence of Human Urine with Benign and Malignant Growth. Cancer Research 9: 672-676, 1949, Rabinowitz.

Ultraviolet Fluorescence in Blood Plasma in the Discrimination of Cancer from Normal. Proc. SPIE vol. 2962, pp. 41-45, 1997. Madhuri et al.

Spectrofluorometric Detection of DMBA-Induced Mouse Skin Carcinoma, Pathology Oncology Research, vol. 5, No. 1 pp. 46-48, 1999 (abstract). Karthikeya et al.

Native Fluorescent Spectroscopy of Blood Plasma in the Characterization of Oral Malignancy, Photochemistry and Photobiology, vol. 78, No. 2, pp. 197-204 (abstract). Madhuri et al.

Characteristic Autofluorescence for Cancer Diagnosis and its Origin. Lasers Surg. Med, vol. 7, pp. 528-532, 1987 (abstract). Yang et al.

Elastin Metabolism and Chemistry: Potential Roles in Lung Development and Structure. Environmental Health Perspectives. vol. 55, pp. 178-191, Rucker et al.

Elastin: molecular description and function. The International Journal of Biochemistry and Cell Biology 31 pp. 261-272, 1999, Debelle et al.

Elastin and the lung. Thorax 41:577-585, 1986. Starcher.

Relation of Serum Elastin Peptide Concentration to age, FEV, smoking habits, Alcohol Consumption, and Protease Inhibitor Phenotype; and Epidemiological Study in Working Men. Thorax 47: 937-942, 1992, Frette et al.

\* cited by examiner

LUNG CANCER DETECTION BY OPTICAL ANALYSIS OF BODY FLUIDS

CROSS-REFERENCE TO RELATED APPLICATIONS

This application is a continuation-in-part of U.S. patent application Ser. No. 12/458,489, filed Jul. 14, 2009 now abandoned, which claims priority to U.S. provisional patent application Ser. No. 61/129,728, filed Jul. 15, 2008. This application is also a continuation-in-part of U.S. patent application Ser. No. 12/285,670, filed Oct. 10, 2008 now U.S. Pat. No. 7,869,033, which is a continuation-in-part of U.S. patent application Ser. No. 12/000,233, filed Dec. 11, 2007 now abandoned, the contents of which are hereby incorporated by reference in their entirety and which is a continuation-in-part of U.S. patent application Ser. No. 11/017,913, filed Dec. 22, 2004, now abandoned, which claims priority to U.S. provisional patent application 60/531,987, filed Dec. 24, 2003. This application also claims priority to India patent application number 587/CHE/2003, filed Jul. 22, 2003 and issued as India patent number 209084 on Aug. 20, 2007.

BACKGROUND OF THE INVENTION

1. Field of the Invention

The present invention relates to the diagnosis of cancer, and particularly to lung cancer detection by optical analysis of body fluids that uses fluorescence spectroscopy to examine samples of blood, urine, and/or sputum to diagnose cancer of the lungs during pre-malignant, early malignant, and advanced malignancy stages.

2. Description of the Related Art

Cancer is often a fatal disease. Modern medicine has developed many modes of treating cancer, including surgical removal of tumors, chemotherapy, immunological therapy, etc. However, the key to effective treatment is early detection.

A number of diagnostic tests are available for determining the presence of cancer. These tests include: surgical biopsy; prostate specific antigen (PSA); DRE tests; computed axial tomography (CAT or CT scans); magnetic resonance imaging (MRI) scans; ultrasound scans; bone scans; positron emission tomography (PET) scans; bone marrow testing; barium swallow tests; endoscopy; cytoscopy; T/Tn antigen tests; mammography; and other tests. Although effective to a greater or lesser extent, each of these tests has advantages and disadvantages.

Some tests, such as PSA, pap smears, and mammography, are specific to particular organs. Others, such as biopsy, endoscopy, bone marrow, and cytoscopy, are invasive tests that often result in considerable discomfort to the patient. Still others, such as CAT scans and MRI scans, are quite expensive and require complex instrumentation.

In particular, cancer of the lung has a very low survival rate (less than 20%) and represents the highest incidence of cancer in most developed countries. Active and passive smoking, along with polluted ambient air, are the main causes of lung cancer. Most of the methods of cancer detection, particularly ultrasound or CAT scans and bronchoscopy, are incapable of early detection. Many scientists and physicians have tried sputum cytology and CT scans coupled with bronchoscopy for early detection, as well as biochemical approaches to identifying and quantifying some lung cancer biomarkers from blood serum. In this approach the sensitivity is less than 70%. Therefore, greater sensitivity is needed to make these techniques viable.

Thus, there is a need for a simple, relatively inexpensive, noninvasive method of screening patients for the presence of cancer, and particularly cancer of the lung, that can be used both for preliminary diagnosis or mass screening of patients, and also during treatment to determine whether cancer has gone into remission. Thus, lung cancer detection by optical analysis of body fluids solving the aforementioned problems is desired.

SUMMARY OF THE INVENTION

The method for lung cancer detection by optical analysis of body fluids relates to analyzing samples of blood, urine and sputum by fluorescence spectroscopy in order to detect the presence of naturally occurring molecules in the fluids that serve as biomarkers indicative of cancer in the human body. The analysis can be carried out based on fluorescence emission spectra, fluorescence excitation spectra and synchronous (emission and excitation) spectra of bio-samples.

In general, optical analysis of body fluids relates to a method of determining the relative concentration of certain bio-molecules in blood urine and sputum samples by fluorescence spectroscopy. The relative concentration of these bio-molecules serves as a marker or screening test to assess the presence and stage of cancer in some organ or tissue of the body, and in some cases, the presence of particular types of cancer in the body. The bio-molecules include various species of porphyrin, flavins (including flavin mononucleotide [FMN], flavin adeno dinucleotide [FAD], and riboflavin), bile components (including biliverdin and bilirubin), tyrosine, tryptophan, and NAD(P)H. The fluorescent spectroscopy techniques include determining intensity maxima in the emission spectra at particular excitation wavelengths characteristic of the bio-molecules, determining intensity maxima in the excitation spectra at particular emission wavelengths characteristic of the bio-molecules, and synchronous scanning of the excitation and emission spectra while maintaining particular offsets in the wavelengths. The method is used to detect the presence of cancer and the relative severity or stage of the disease both as a diagnostic screening method and for evaluating the progress of treatment.

The blood samples may be blood plasma and/or extracts from blood cells. The urine samples may be fresh urine samples, or extracts from urine. The apparatus used may include either an incoherent light source, such as a lamp, or a coherent light source, such as a laser. The excitation wavelength may be determined by an interference filter, a notch filter, or a grating. The emission intensity may be detected by a photodiode, photomultiplier tube, or CCD array.

The present inventors have discovered that the method for cancer detection by optical analysis of body fluids can particularly be used to detect the presence of lung cancer, including identifying early malignant and advanced malignancy stages, and for screening individuals, e.g., heavy smokers, who are at risk for developing lung cancer or in pre-malignant stages. This has become possible through the present inventors' discovery of fluorescent intensity bands particularly characteristic of lung cancer, which the inventors have assigned to elastin, collagen, and or pyridoxine, and to a method of determining the significance of these bands in combination with the intensities assigned to the other biomarkers listed above.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
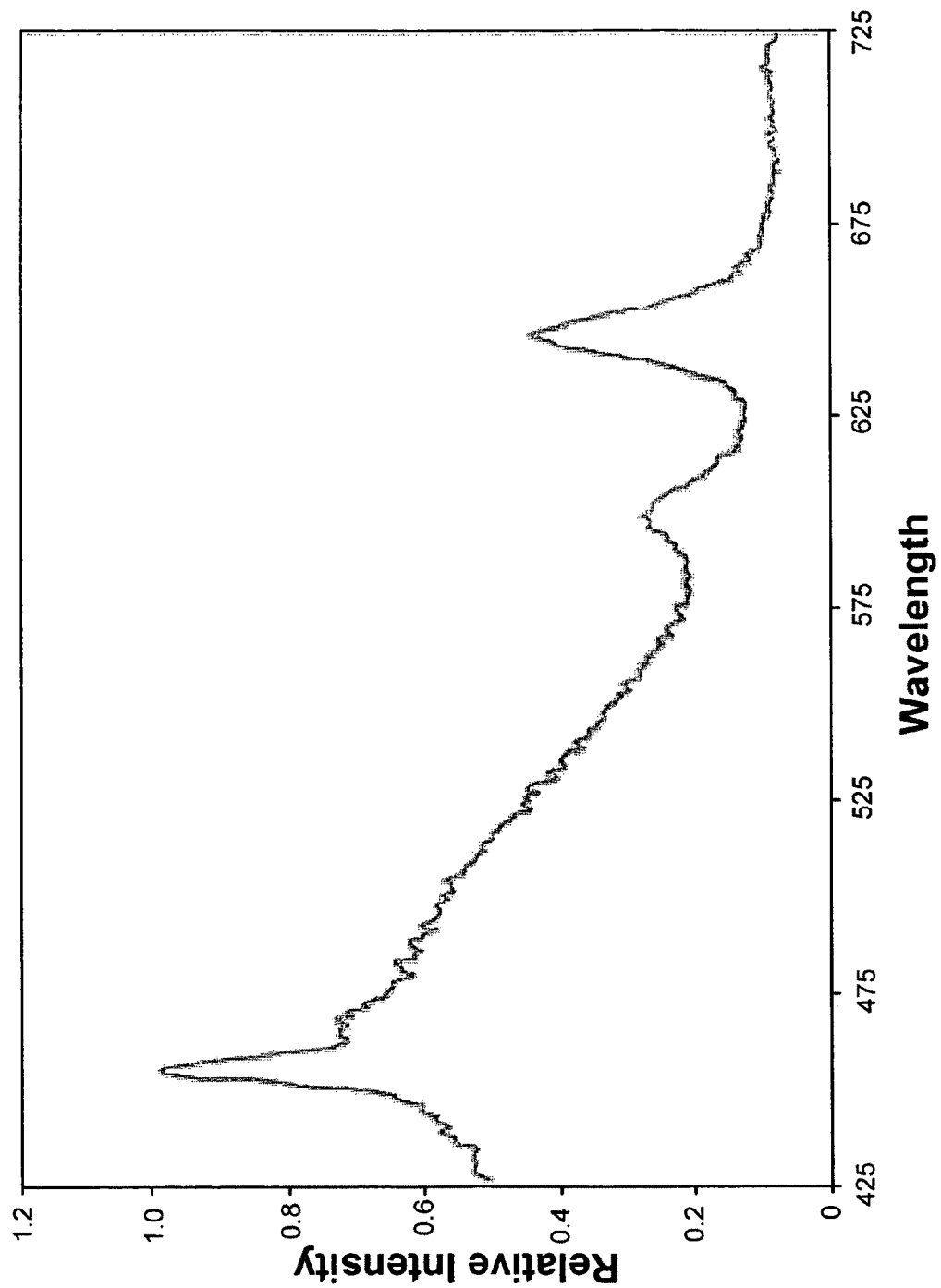
FIG. 1 shows the fluorescent emission spectrum at an excitation wavelength of 400 nm of a sample extract of the formed elements of blood of a healthy person.

In general, cancer detection by optical analysis of body fluids is a method of determining the relative concentration of certain bio-molecules in blood, sputum and urine samples by fluorescent spectroscopy. The relative concentration of these bio-molecules serves as a marker or screening test to assess the presence and stage of cancer in some organ or tissue of the body, and in some cases, the presence of particular types of cancer in the body. The bio-molecules include various species of porphyrin, riboflavin, bile components, bilirubin, tryptophan, tyrosine, elastin, collagen, pyrodoxin, NAD(P)H, biliverdin, and flavins. The fluorescent spectrography techniques include determining intensity maxima in the emission spectra at particular excitation wavelengths characteristic of the bio-molecules, determining intensity maxima in the excitation spectra at particular emission wavelengths characteristic of the bio-molecules, and synchronous scanning of the excitation and emission spectra while maintaining particular offsets in the wavelengths. The method is used to detect the presence of cancer and the relative severity or stage of the disease both as a diagnostic screening method and for evaluating the progress of treatment.

The method may be carried out using any fluorescent spectrography apparatus known in the art. The optical source may be a lamp, such as a halogen lamp, a mercury lamp, a xenon lamp, a tungsten lamp, or other lamp used in fluorescent spectrographs. Alternatively, the optical source may be a coherent light source, such as a diode laser, a helium-cadmium laser, a frequency-doubled, tunable titanium-sapphire laser, or a tunable dye laser. The excitation wavelength may be determined by an interference filter, a notch filter, a slit and grating, or by any other wavelength determining means. Optical detection may be by a photodiode, a photomultiplier tube, an avalanche diode, a CCD array, or any other conventional detector.

Fluorescent spectrography is based upon the phenomenon that certain molecules absorb light at certain frequencies or wavelengths to reach an excited energy level, and subsequently decay to a lower energy state by fluorescing at particular wavelengths. Detectors are capable of detecting this fluorescence with great sensitivity, down to parts in a billion, or even from a single molecule.

The optical analysis of body fluids, as set forth herein, rests upon the identification by the present inventors of certain fluorescence excitation-emission wavelengths characteristic of the bio-molecules mentioned above that may be found in body fluids, such as blood and urine. The optical analysis also rests upon the recognition by the present inventors that the relative proportions of such bio-molecules in blood and urine are affected by the presence of cancerous conditions in the body and the stage of development of the cancerous condition. A fuller description of the general method for optical analysis of body fluids for the detection of cancer is given in U.S. patent application Ser. No. 12/285,670, filed Oct. 10, 2008 by Vadivel Masilamani and Masilamani Elangovan (two of the present co-inventors), the contents of which are hereby incorporated by reference in its entirety.

The present inventors have discovered that the method for cancer detection by optical analysis of body fluids can particularly be used to detect the presence of lung cancer, including identifying early malignant and advanced malignancy stages, and for screening individuals, e.g., heavy smokers, who are at risk for developing lung cancer or in pre-malignant stages. This has become possible through the present inventors' discovery of fluorescent intensity bands particularly characteristic of lung cancer, which the inventors have assigned to elastin, collagen, and or pyridoxine, and to a method of determining the significance of these bands in combination with the intensities assigned to the other biomarkers listed above. The method will now be explained by reference to particular examples.

Example 1

A disposable syringe is used to uptake 5 ml of venous blood from the subject. The blood is placed in a sterile vial containing ethylenediaminetetraacetic acid (EDTA) anticoagulant. The blood is centrifuged at 4000 rpm for 15 minutes, and the supernatant plasma is separated out and collected in a sterile vial. The formed elements containing mostly cells, such as erythrocytes, are treated with acetone in the ratio of 1:2 (i.e., to 1 ml of formed elements, 2 ml of acetone). The sample is vigorously shaken 100 times and then centrifuged at 4000 rpm for 15 minutes.

The supernatant thus obtained is a clear solution containing the bio-molecules that are tumor markers. It is subjected to the optical analysis as described before. The wavelength of excitation is fixed at 400 nm by adjusting the interference filter or grating, and the fluorescence emission spectrum is obtained in the range of 425 to 720 nm.

Figure 2:
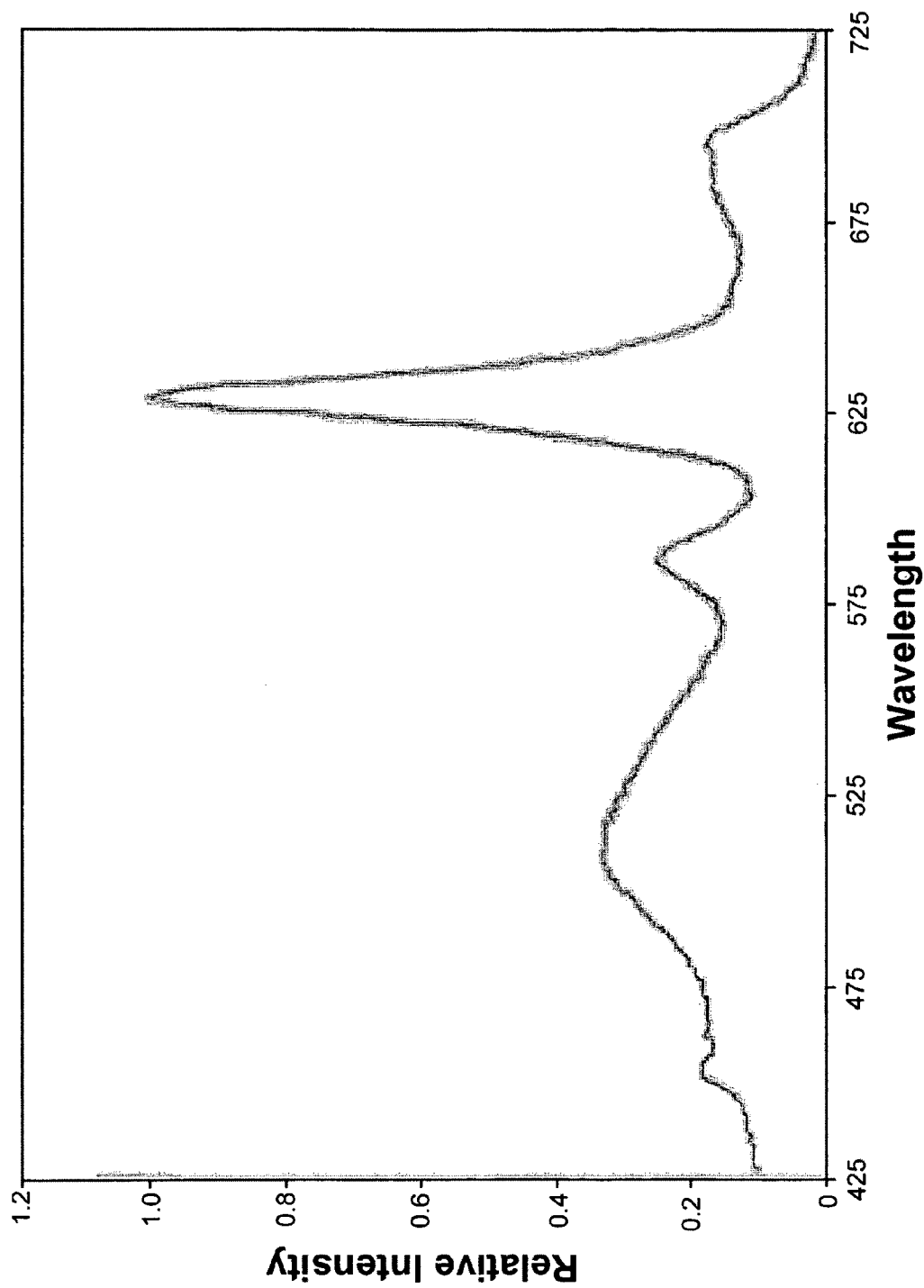
FIG. 2 shows the fluorescent emission spectra at an excitation wavelength of 400 nm of a sample extract of the formed elements of blood of a diseased lung cancer patient (advanced stage).

A typical result is shown in FIG. 1 for a sample from a healthy individual, and in FIG. 2 for a sample from an individual with cancer. The spectrum consists of 5 bands: (1) around 460 nm, due to Raman scattering of acetone; (2) a fluorescence band at around 505 nm, most probably due to riboflavin and bile components; (3) a fluorescence band at around 585 nm due to anionic species of porphyrin; (4) a fluorescence band at around 630 nm due to neutral species of porphyrin; and (5) a fluorescence band at around 695 nm due to cationic species of porphyrin.

The intensities of the bands are measured and denoted as $I_{460}$, $I_{505}$, $I_{585}$, $I_{630}$, and $I_{695}$. The ratios of the intensities are denoted, for example, as:

Ratio $(R_1) = (I_{630}/I_{585})$

If $R_1 < 1.5$, it implies that the patient is healthy. If $1.5 < R_1 < 2.25$, it implies that the patient is at high risk of cancer. If $2.25 < R_1 < 3$, it implies that the patient is at early stages of lung cancer. If $R_1 > 3$, it indicates an advanced stage of lung cancer. Other ratios of interest include the following:

$(R_2) = I_{695}/I_{585}$
$(R_3) = I_{630}/I_{505}$
$(R_4) = I_{585}/I_{460}$
$(R_5) = I_{505}/I_{460}$

These fluorescence intensity ratio parameters are proportional to the ratio of concentration of above cited bio-molecules. These are in different ratio for healthy and diseased samples. They are summarized in Table 1.

TABLE I

Fluorescence Intensity Ratio for Formed Elements

| Ratio | Healthy | Pre-Malignant | Early Cancer | Advanced Cancer | Contrast Param. |
|---|---|---|---|---|---|
| $R_1$ | <1.5 | 2.25 > $R_1$ > 1.5 | 3 > R1 > 2.25 | >3.0 | 2 |
| $R_2$ | 0.4 ± 0.1 | 0.5 ± 0.1 | 0.8 ± 0.2 | 1.5 ± 0.5 | 4 |

TABLE I-continued

Fluorescence Intensity Ratio for Formed Elements

| Ratio | Healthy | Pre-Malignant | Early Cancer | Advanced Cancer | Contrast Param. |
|---|---|---|---|---|---|
| $R_3$ | 0.6 ± 0.2 | 1 ± 0.25 | 1.25 ± 0.25 | 2 ± 0.5 | 3 |
| $R_4$ | 0.3 ± 0.1 | 0.5 ± 0.1 | 0.7 ± 0.1 | 1 ± 0.2 | 3.3 |
| $R_5$ | 0.5 ± 0.1 | 0.7 ± 0.1 | 0.9 ± 0.1 | 1.2 ± 0.2 | 2.2 |

$R_1$, $R_2$ and $R_3$ depend upon the concentration of porphyrin, a bio-molecule involved in heme metabolism. This is found at higher concentration in the tissue of cancer patients than in healthy subjects because of abnormal cell proliferation in the cancer patients. This is, in general, is the basis for laser-based photodynamic therapy, which is in practice all over the world.

Figure 3:
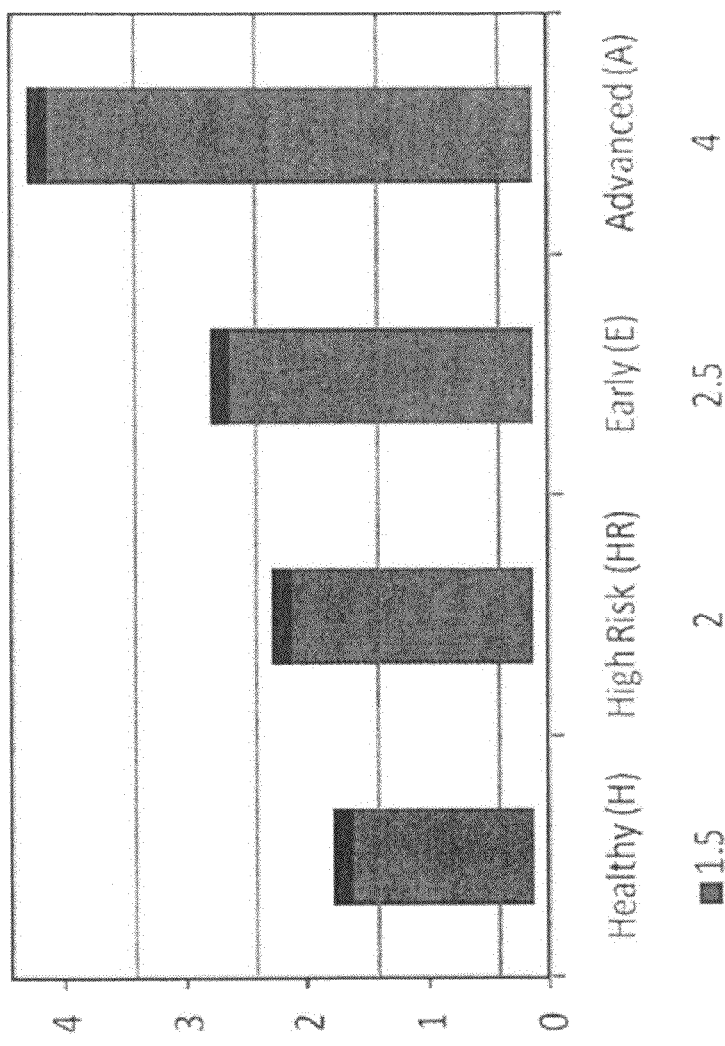
FIG. 3 shows a histogram or bar chart showing the relative ratios of the fluorescence emission spectra intensity of neutral porphyrin to anionic porphyrin ($I_{630}/I_{585}$) for healthy persons, persons at high risk for cancer, persons in early malignancy, and persons in advanced stage of malignancy.

In the present method, we are concerned with the concentration of porphyrin carried from the tissue into the blood stream and excreted through urine. If the concentration of this fluorophore is higher, then the tumor activity or the tumor volume is also higher. This aspect is more explicitly brought out by the bar chart in FIG. 3.

Example 2

Figure 4:
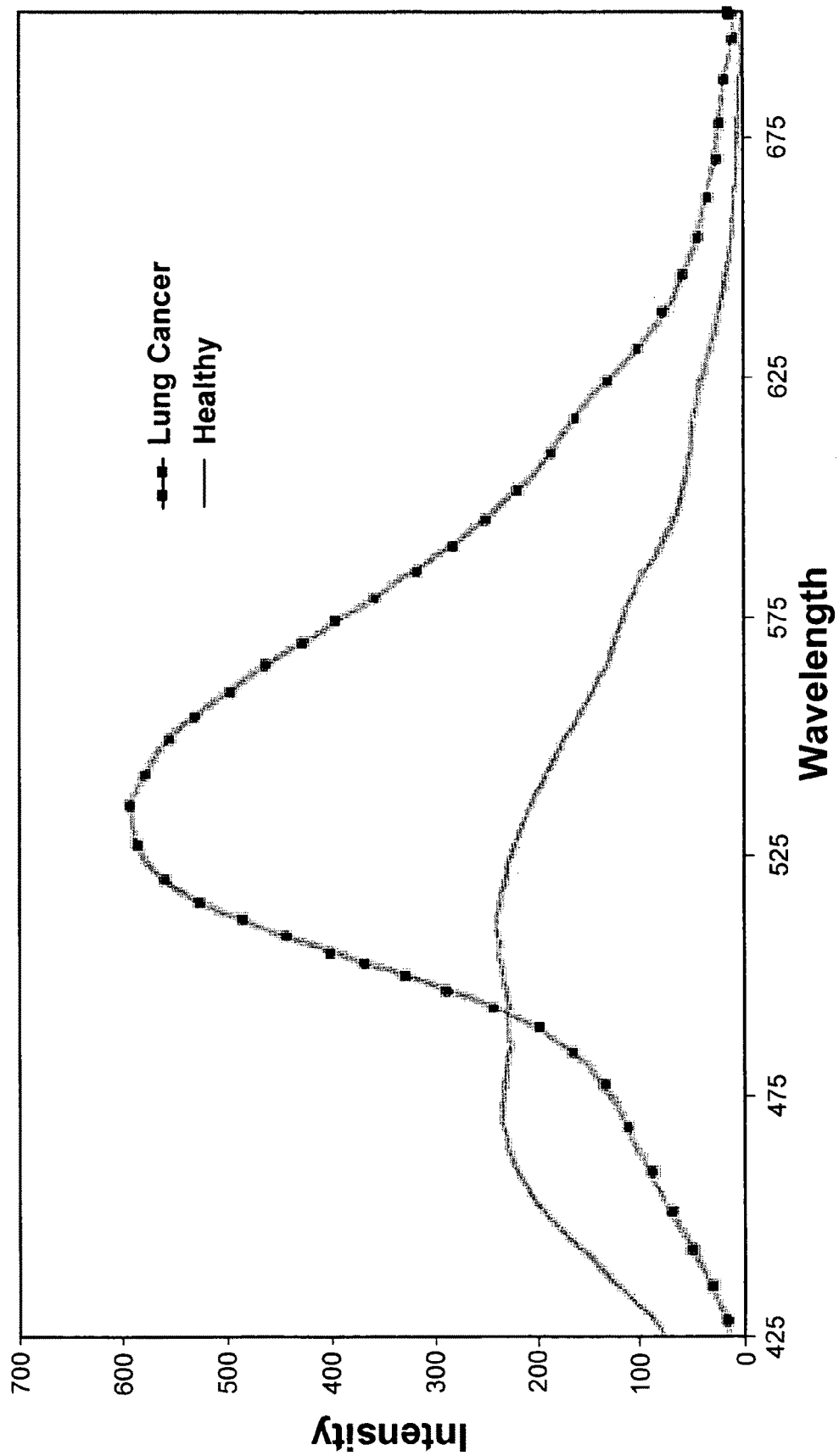
FIG. 4 shows the fluorescence emission spectra at an excitation wavelength of 400 nm of the urine sample of a lung cancer patient compared to that of a healthy subject.

Urine samples are prepared for analysis as follows. The subject is required to give the first voided urine in a sterile vial after 48 hours of strict abstinence from non-essential medicines (including herbal and ayurvedic), spicy meals, and meats. 2 ml of urine is dropped in a quartz cuvette. The excitation wavelength is set at 400 nm, and the fluorescence spectrum from 425 to 700 nm is obtained. Exemplary spectra for a healthy individual and a lung cancer patient are shown in FIG. 4. Among the many bands, we ignore all except the 470, 520, 550, and 620 nm bands, which are consistent. A set of cancer-defining ratio parameters is given in Table II.

TABLE II

Ratio Parameters $R_7$ through $R_9$

| Ratio Parameter | Normal | Pre Malignancy of lung | Early Cancer of lung | Advanced stage Lung Cancer |
|---|---|---|---|---|
| $R_6 = (I_{520}/I_{470})$ | <1 | 1.2-1.4 | 1.4-1.6 | >1.6 |
| $R_7 = (I_{620}/I_{470})$ | <0.3 | 0.3-0.5 | 0.5-0.8 | >0.8 |
| $R_8 = (I_{550}/I_{470})$ | <0.4 | 0.6-0.8 | 0.8-1.0 | >1.0 |

It will be noted that the FES peak shifts from 500 nm to 535 nm as the disease progress from pre-malignant to early stage to advanced stage of malignancy. This shift itself is a very clear indicator of disease.

Example 3

Fluorescence excitation spectra of the samples were obtained where the emission grating is fixed and the excitation grating is rotated to obtain the excitation spectra, which is similar to, but not identical to, the absorption spectra. With suitable modifications in the system, one can get Synchronous Spectra (SS). Here, the excitation grating and emission grating are set at a wavelength difference of 70 nm or 30 nm, as required for the specific analysis. That is, when one grating is at 200 nm, the other is set at 270 nm, with the offset wavelength difference being 70 nm. Then, both gratings are synchronously scanned. The fluorescence obtained with the excitation of 200 nm is collected from 270 nm onwards. Then the excitation grating moves to 210 and synchronously the emission grating moves to 280 and collects fluorescence; this kind of synchronous scanning can go on up to 600 nm.

This is a compounded spectrum of fluorescence emission and excitation bands of many molecules, but each molecule being excited individually. It gives a better resolution and identification of weakly fluorescing, submerged fluorophores. This becomes an additional window of analysis.

The blood plasma samples are prepared as outlined above and placed in the cuvette as before, and taken through optical analysis.

In addition, early morning deep-coughed sputum or induced sputum samples were collected by trained technicians from healthy persons and cancer-diseased patients, and also from heavy smokers. These samples were also subjected to fluorescence emission, excitation and synchronous spectra like other samples.

Spectra obtained for such samples show distinct and marked differences between healthy and diseased body fluid.

Figure 5:
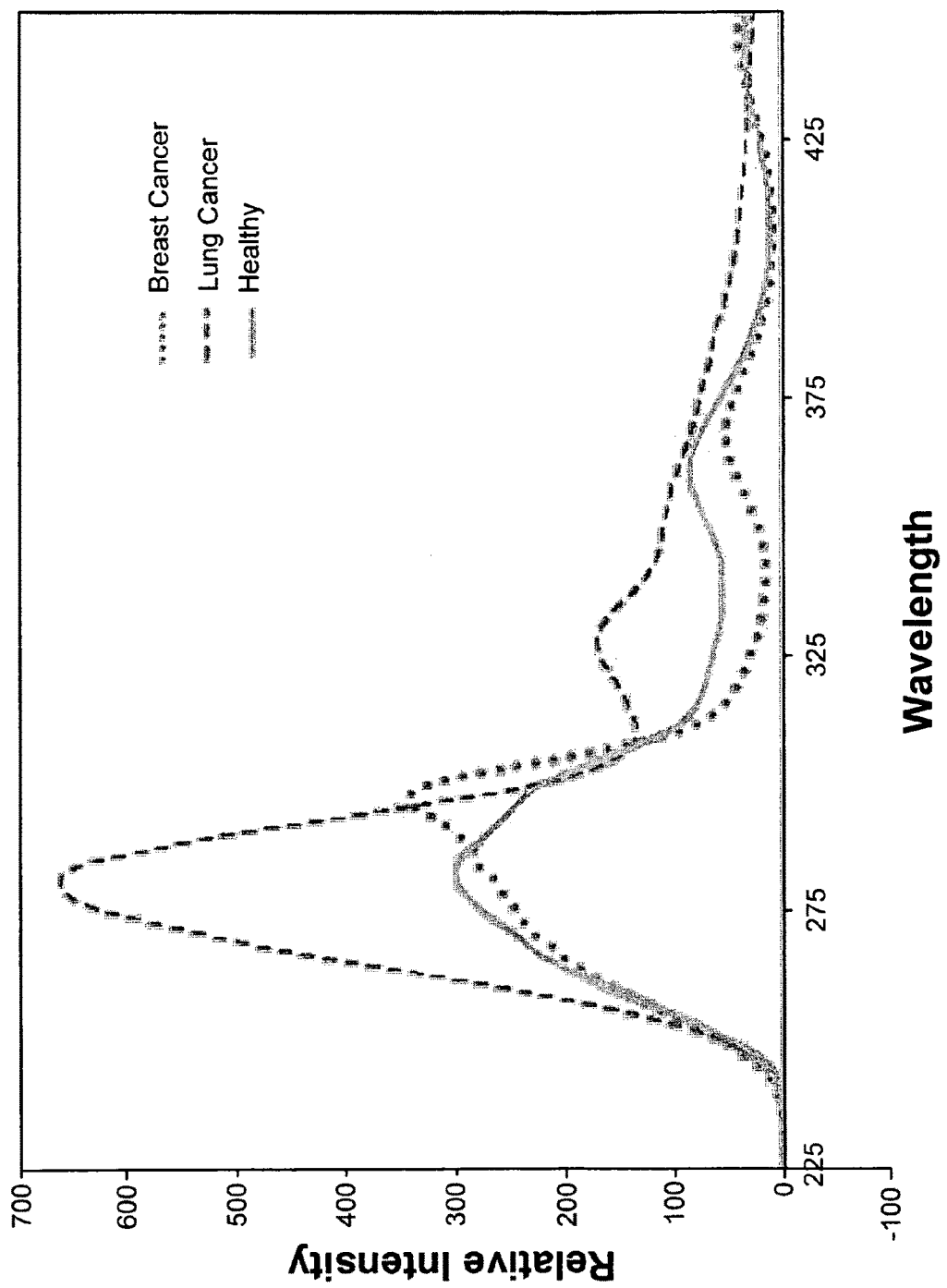
FIG. 5 shows the synchronous spectra (SS) with an offset of 70 nm of blood plasma samples for a healthy subject, a breast cancer patient and a lung cancer patient.

With reference to the SS of blood plasma, with an offset of 70 nm as in FIG. 5, there were well-defined bands around 290 nm, 365 nm, and 450 nm. As blood plasma contains a host of free and enzyme-bound fluorophores (bio-molecules), we can only tentatively assign the bands to the fluorophores. Out of these, the 290 nm band is due tryptophan, the 365 nm band is most likely due to NAD(P)H, and the 450 nm band is due to flavins. Comparing the healthy and diseased spectra, one can notice that these biomolecules are out of proportion in diseased blood plasma, as shown in the comparison spectra of FIGS. 5 and 6.

For example, the ratio of the band at 290 nm (due to tryptophan) and at 270 nm (due to tyrosine) is about 0.8 for the healthy person, about 1.2 for the advanced breast cancer patient, and about 1 for an early lung cancer patient (so the contrast parameter is 1.5). Further, the intensity of the 290 nm band is very high for diseased plasma.

There is also a totally unique fluorescent biomarker exclusively indicative of lung cancer. This appears at 327 nm in the synchronous spectra with an offset of 70 nm. This biomarker is totally absent in normal, healthy persons, and is also totally absent in all other cancers of different etiology (compare the spectrum of the breast cancer patient with the lung cancer patient in FIG. 5). Note it is weakly present in early lung cancer and quite strong for advanced lung cancer (compare the early malignant lung cancer spectrum with the advanced lung cancer spectrum in FIG. 6). From this point of view, this biomarker at 327 nm is an exclusive and a specific indicator of lung cancer. This biomarker has a fluorescence emission peak at 390 nm. So, the present inventors believe it to be most likely due to the structural protein elastin, and to some extent due to collagen and pyridoxine.

Example 4

What is all the more important is that this particular biomarker is also present very distinctly not only in the plasma of lung cancer patients, but also in the sputum and tissue of lung cancer patients. FIG. 7 shows the synchronous spectra with offset of 70 nm of sputum and tumor tissue from the same advanced lung cancer patient of FIG. 6. The similarity in the spectra is quite obvious, i.e., that both have the same shape and relative intensities of bands at 290 nm (due to tryptophan), at 327 nm (due to elastin) and at 450 nm (due to flavin), so that the bands of interest are about the same. However, there is a blue shift of about 10 nm for the tissue due to the difference in the environment. This establishes clearly that the SS of plasma and the sputum sample of the cancer patient is equivalent to that of the lung cancer tissue of the same patient. In other words, the lung cancer tissue is the repository of all biomolecules released in the blood and sputum.

Figure 17B:
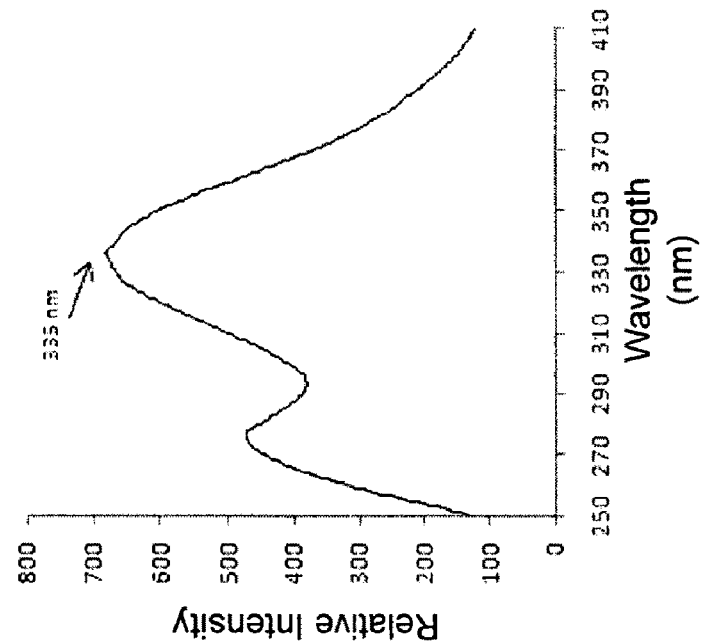
FIG. 17B shows the synchronous spectrum of a known sample of elastin.
Figure 17A:
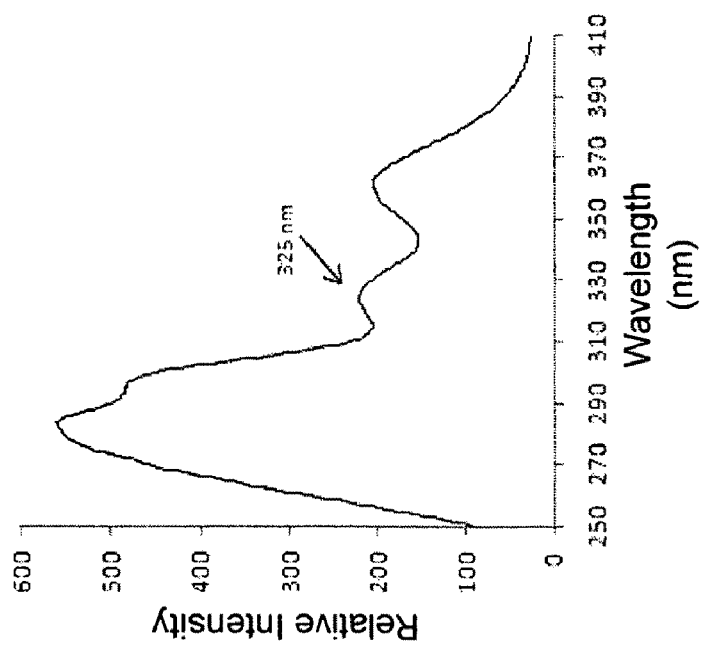
FIG. 17A shows the synchronous spectrum of a plasma sample of a lung cancer patient.
Figure 17D:
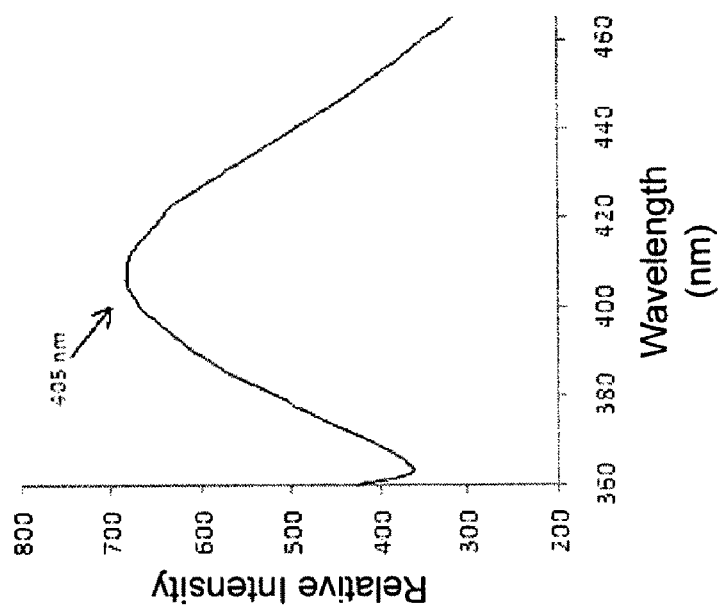
FIG. 17D shows the fluorescence emission spectrum at an excitation wavelength of 327 nm of the known sample of elastin of FIG. 17B.
Figure 17C:
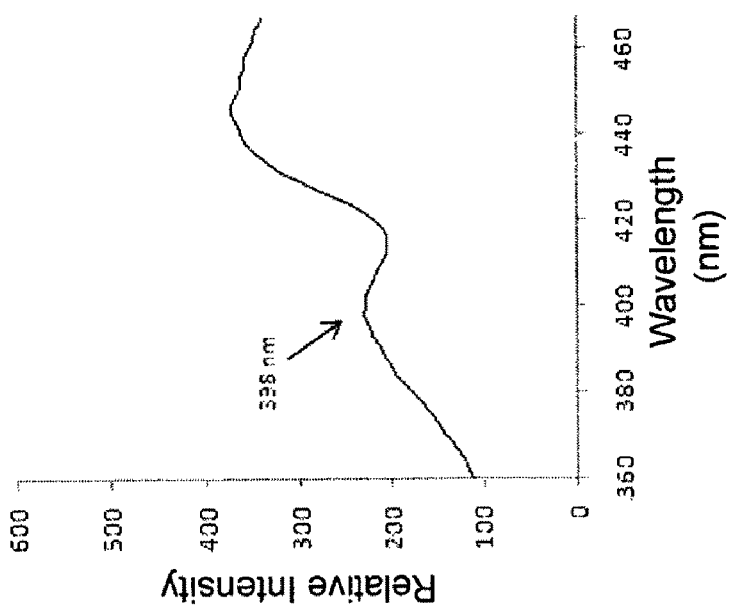
FIG. 17C shows the fluorescence emission spectrum (FES) at an excitation wavelength of 327 nm of the lung cancer plasma of FIG. 17A.

For any fluorophore, the fluorescence emission and excitation bands, both put together as a matched pair, represent a unique set of fingerprints. In order to identify the spectral biomarker, the SS and fluorescence emission spectra (FES) of purified bovine neck elastin, calfskin collagen, NADPH and flavin were obtained, each individually dissolved in PBS at a concentration of 1 mg/ml. Out of these, only the SS and FES of elastin had the one-to-one correspondence with the spectra of lung cancer samples. FIG. 17A shows the SS of plasma of the patient with SCC (lung cancer) and FIG. 17B shows the SS of elastin with a most prominent band at 275, due to the tryptophan moiety and a characteristic band of elastin at around 330 nm. When excitation was performed at 327 nm, the FES for plasma showed a peak that occurred at about 400 nm, as shown in FIG. 17C. In a similar fashion, when excitation was performed for elastin at 327 nm, FES showed a peak that occurred at about 400 nm, indicating very good spectral matching.

It should be noted that there is a small spectral difference of about 5 nm. This is because the environment of a plasma could not be readily simulated, and also because there are strong spectral neighbors on either side of elastin, which influences the spectrum of elastin. It should be further noted that the band at 450 nm in FIG. 17C (in the FES of plasma of the lung cancer patient), is due to NADPH, which has a corresponding excitation band at 350 nm, as shown in FIG. 17A. These two are absent in FIGS. 17B and 17D, because these two Figures represent the SES and FES of pure elastin.

Example 5

Figure 6:
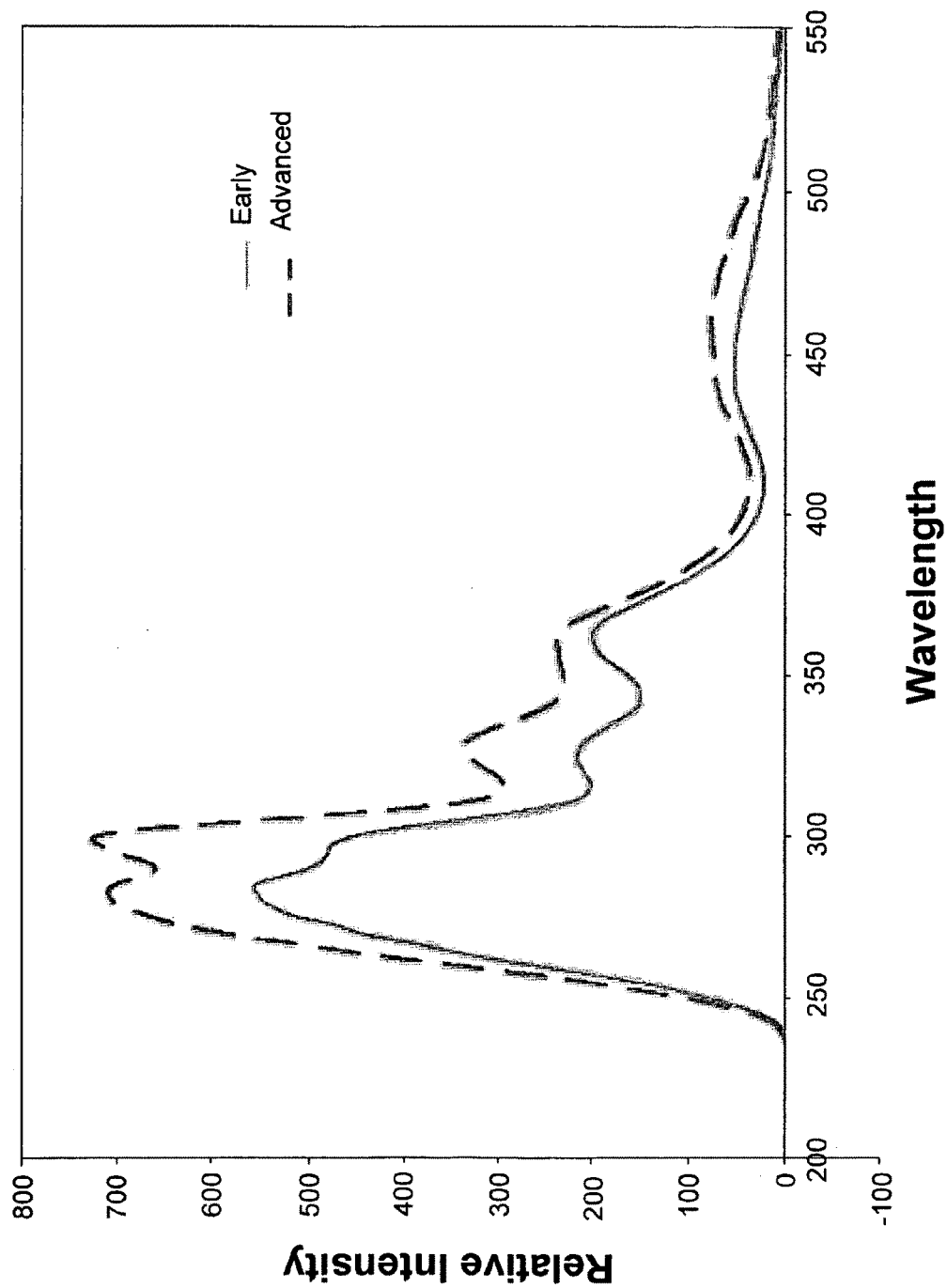
FIG. 6 shows the synchronous spectra with an offset of 70 nm of blood plasma samples for an early malignant stage lung cancer patient and an advanced stage lung cancer patient.
Figure 7:
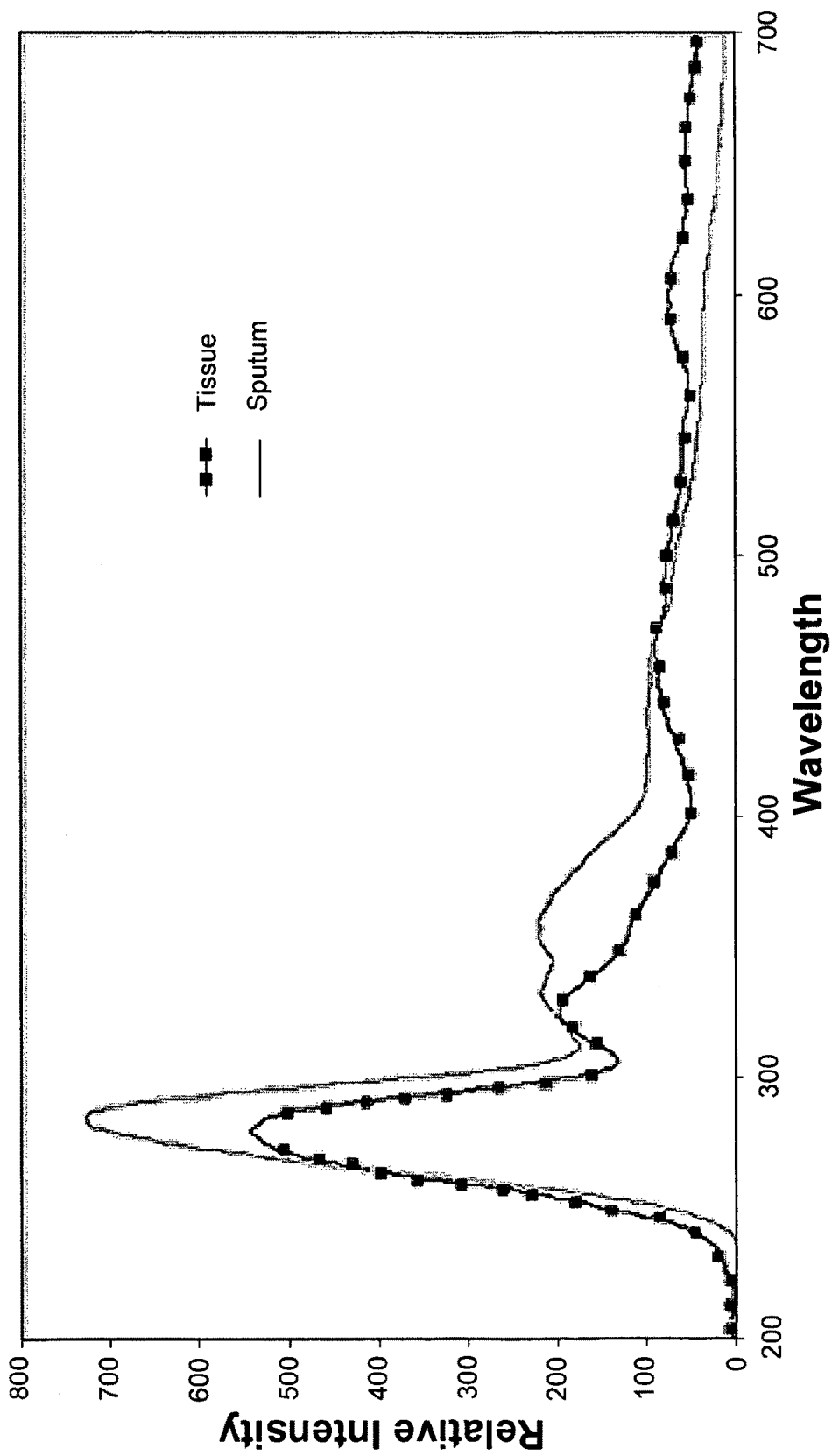
FIG. 7 shows the synchronous spectra with an offset of 70 nm of a tissue sample and a sputum sample for the same advanced lung cancer patient.
Figure 8:
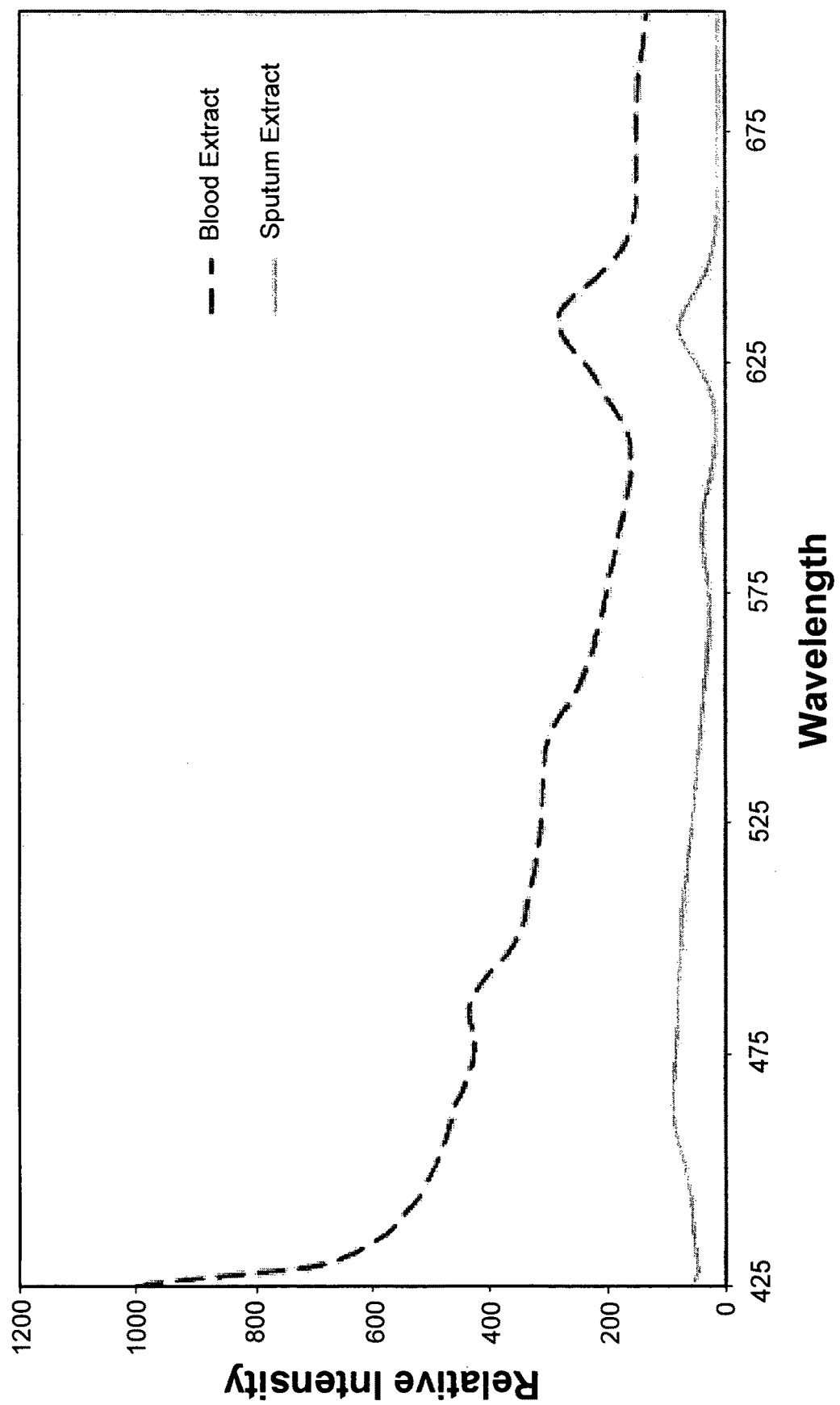
FIG. 8 shows the fluorescence emission spectra at an excitation wavelength of 400 nm of sputum and a sample extract of the formed elements of blood of the same lung cancer patient.

FIG. 8 shows the fluorescence emission spectra (excitation at 400 nm) of the sputum and acetone extract of formed elements of the blood of the same lung cancer patient as FIGS. 6 and 7. The similarity in the spectra again is quite obvious, that both have the same shape and relative intensities of bands at 480 nm (due to NADH), at 535 nm (due to flavin and bilirubin) and also at 310 nm (due to porphyrin), so that the ratio of intensities of the bands of interest are about the same. This reinforces clearly that the visible range spectra of sputum and blood components are equivalent.

Example 6

Figure 9:
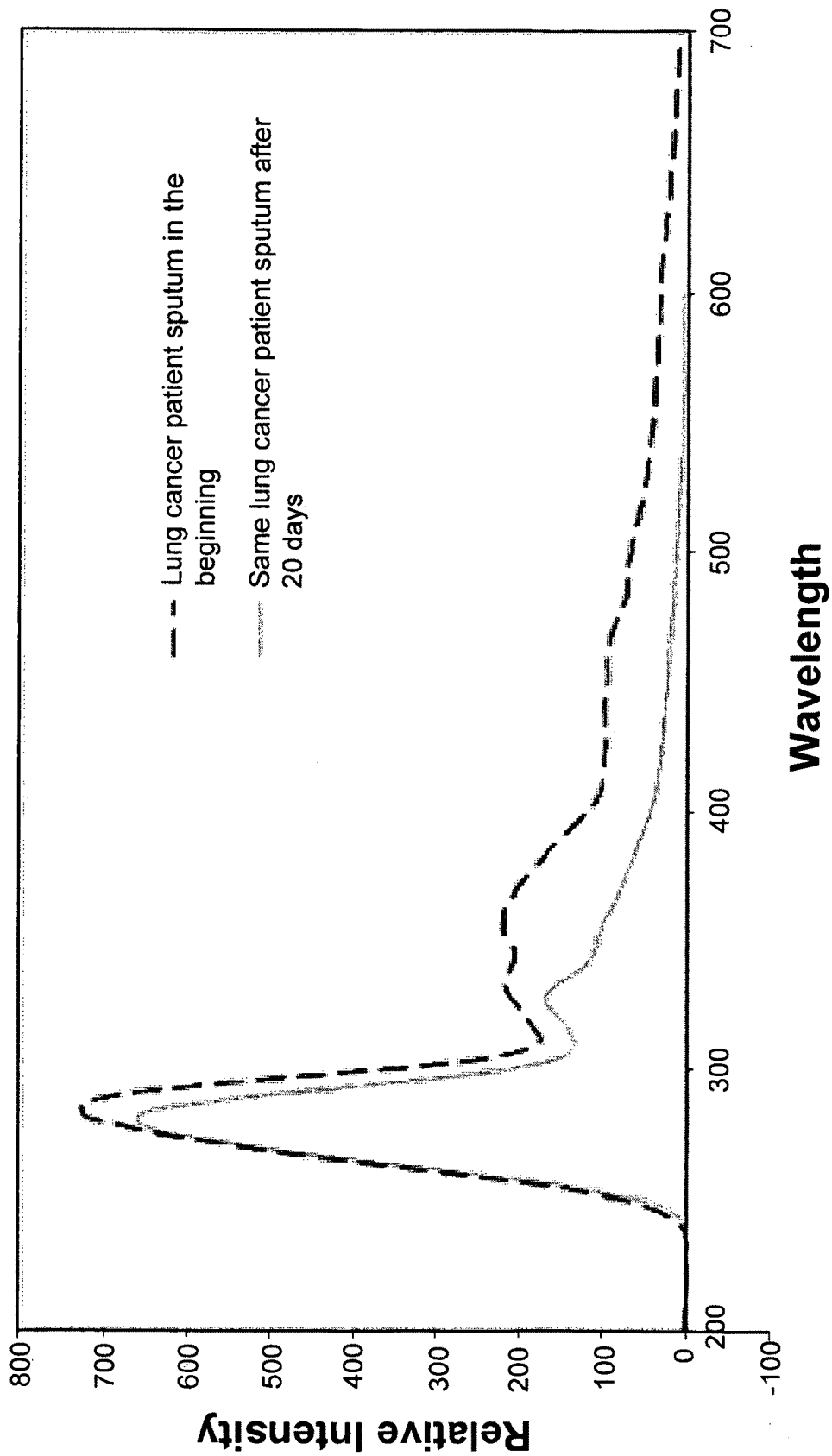
FIG. 9 shows the synchronous spectra with an offset of 70 nm of sputum samples at the beginning and at the end of a 20-day period of the same lung cancer patient.
Figure 10:
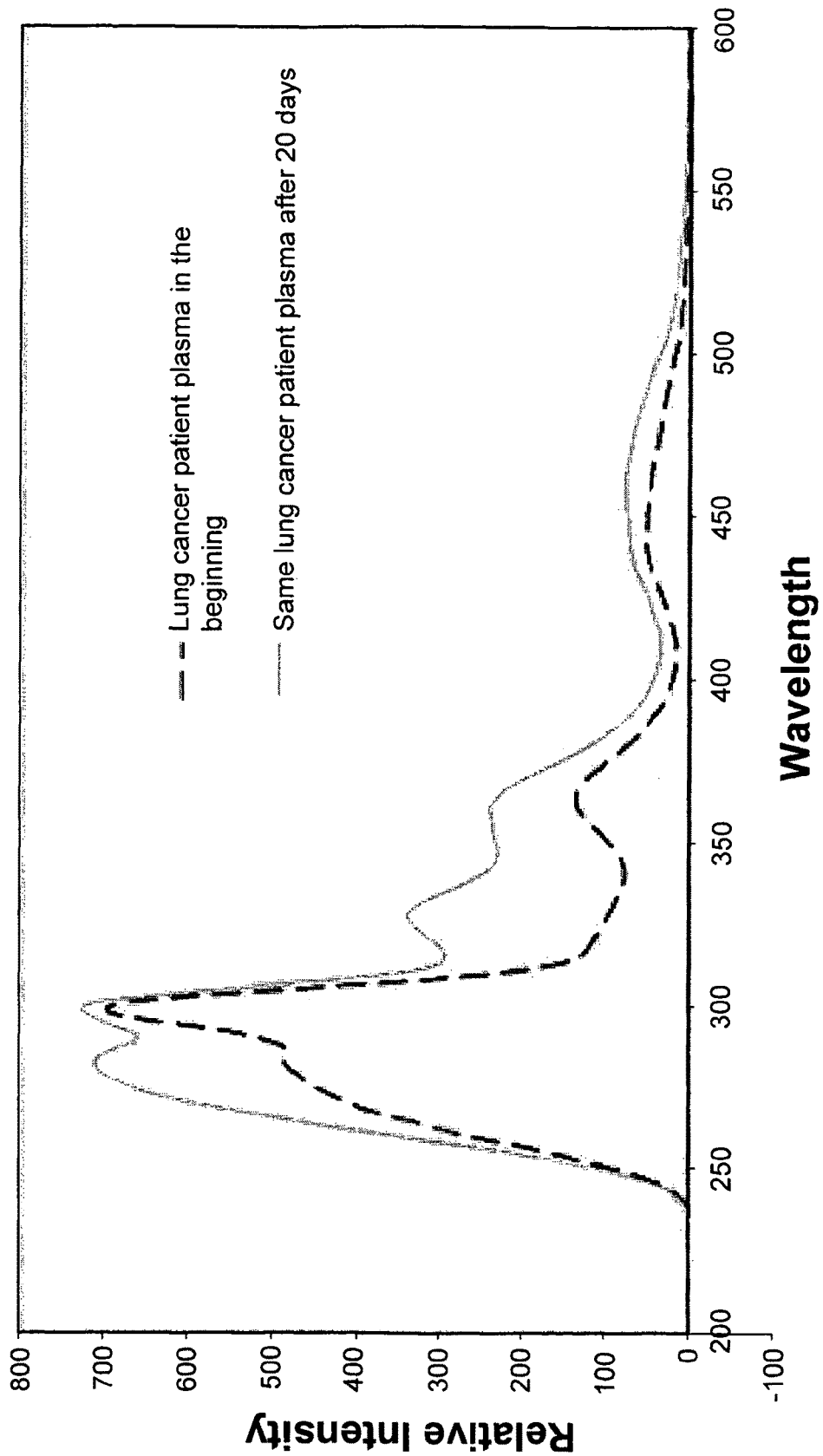
FIG. 10 shows the synchronous spectra with an offset of 70 nm of blood plasma samples at the beginning and at the end of a 20-day period of the same lung cancer patient.

In order to demonstrate the efficacy of this technique, two spectra, FIG. 9 (for sputum) and FIG. 10 (for plasma), are given, which were obtained from the same patient in a span of 20 days. With focus on the band at 327 nm, indicating the elevation of the structural proteins, it can be seen that the disease has become worse in a span of 20 days, and by this technique the evolution of disease could be monitored, either by analyzing plasma or sputum, but preferably both.

Example 7

It has been well established that heavy smokers have 10- to 20-fold enhanced risk factors for lung cancers. Hence, it is significant that such a segment of the population can be effectively screened by optical analysis of sputum and urine, as shown below.

Figure 11:
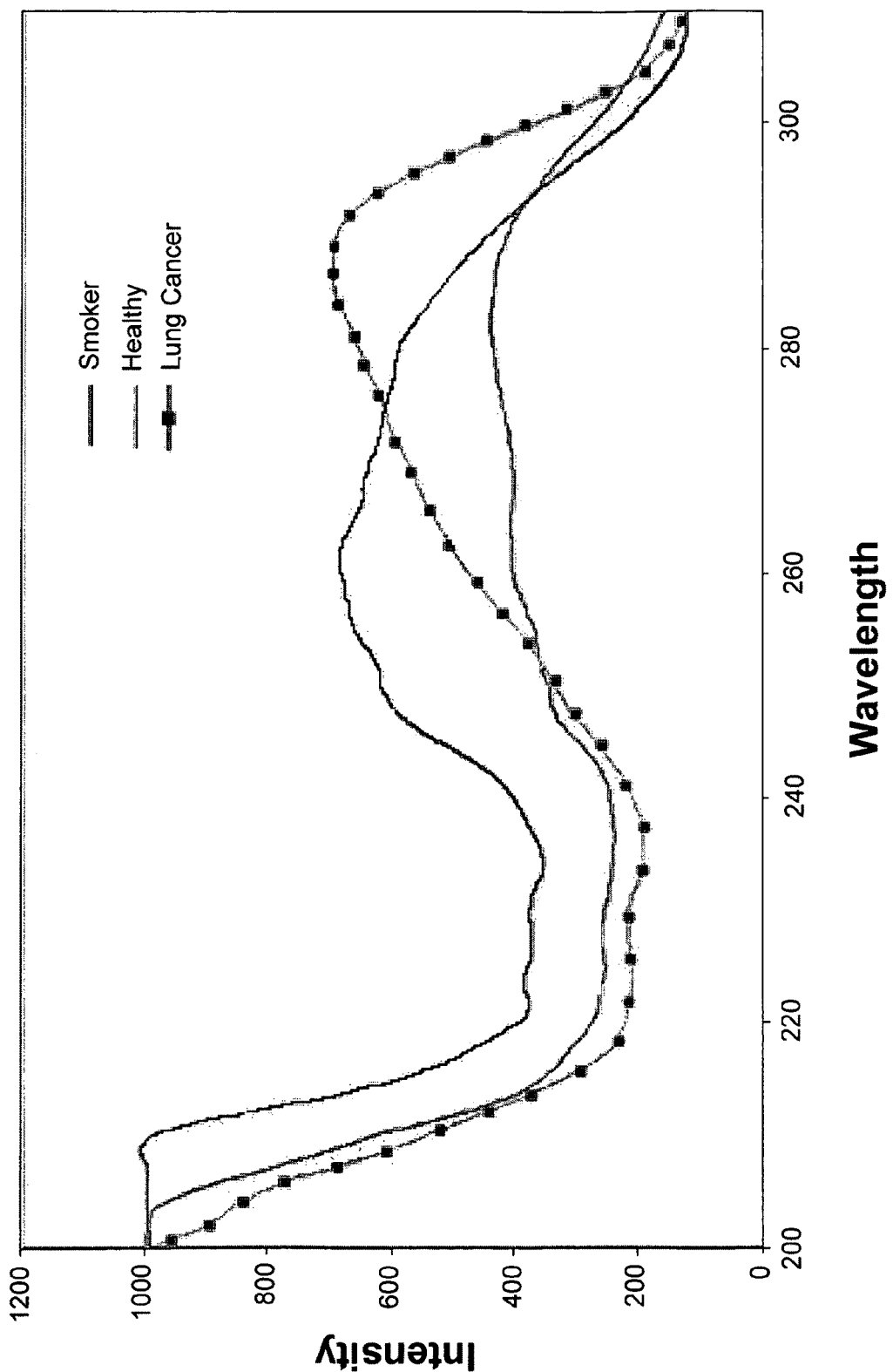
FIG. 11 shows the fluorescence excitation spectrum at an emission wavelength of 340 nm of the sputum samples of three persons: one a healthy person, another person a smoker, and the third person a lung cancer patient.

FIG. 11 gives the fluorescence excitation spectra (with emission at 340 nm) of sputum of three persons: a non-smoker, a heavy smoker and a lung cancer patient. The elevation of tryptophan (the 280 nm peak) in comparison with tyrosine (the 260 nm peak) is an indication of malignancy. The ratio between these two amino acids is about 1:0.8 for the healthy person, and 2:1 for the lung cancer patient. The heavy smoker is somewhere in between, with the ratio being 1.3:1.

Also, it is noted that the peaks of these spectra shift from 260 nm for the healthy person, to 280 nm for the heavy smoker, and to 290 nm for the lung cancer patient. That is to say, the heavy smoker has moved from the domain of normalcy and is now close to the cancerous region.

Example 8

Figure 12:
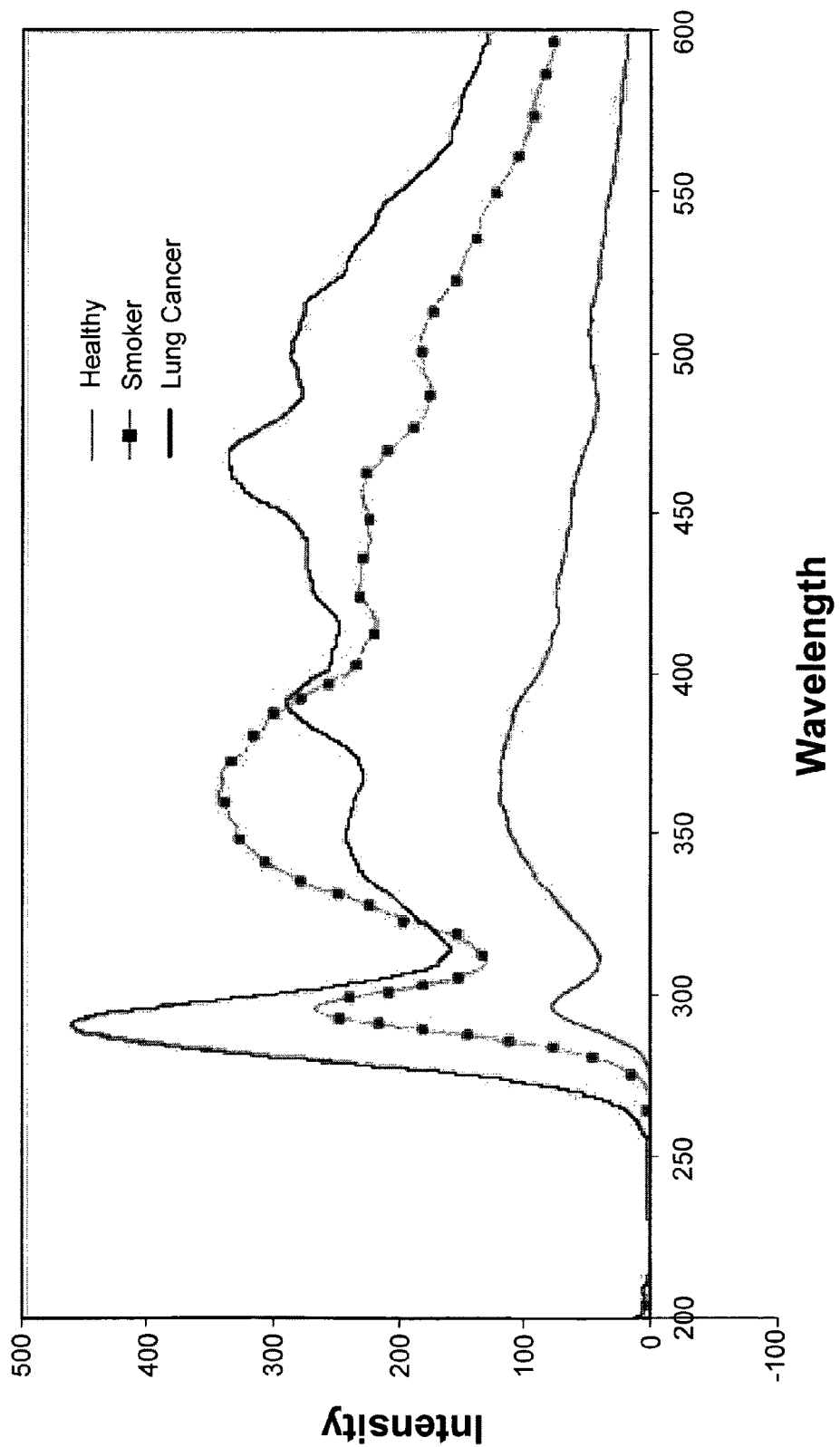
FIG. 12 shows the synchronous spectra with an offset of 30 nm of the sputum samples of three persons: one a healthy person (bottom curve), the second person a heavy smoker (middle), and the third person a lung cancer patient (top).

FIG. 12 gives the synchronous spectra (with an offset of 30 nm) of the sputum of three persons: a non-smoker (bottom curve), a heavy smoker (middle), and a lung cancer patient (top). The elevation of tryptophan and tyrosine (with a peak around 300 nm), as can be noticed here, is an indication of malignancy. The ratio between the maximum intensity at 300 nm and the minimum intensity at 320 nm is about 1.5:1 for the non-smoker, 2:1 for the heavy smoker, and 3:1 for the lung cancer patient.

Another important ratio parameter is $I_{450}/I_{355}$ (flavin vs. NADPH), which is about 0.6:1 for the non-smoker, and about 0.8:1 for the smoker, but about 1.2:1 for the lung cancer patient.

Example 9

Figure 13:
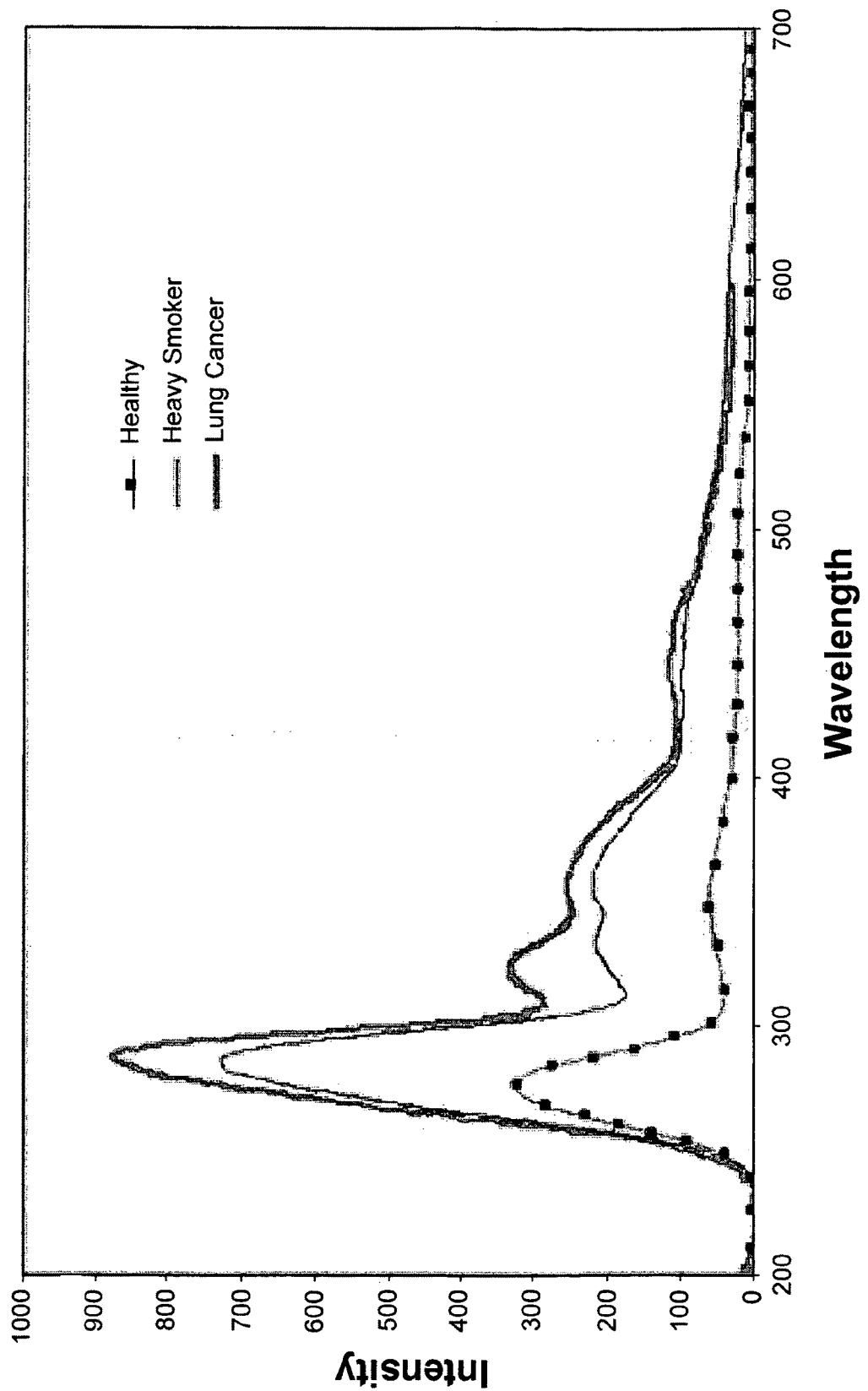
FIG. 13 shows the synchronous spectra with an offset of 70 nm of the sputum samples of three persons: one a healthy person (bottom curve), the second person a heavy smoker (middle), and the third person a lung cancer patient (top).

FIG. 13 gives the synchronous spectra (with an offset of 70 nm) of the sputum of three persons: a non-smoker (bottom curve), a heavy smoker (middle), and a lung cancer patient (top). The elevation of tryptophan (with a peak around 290 nm), as can be noticed here, is an indication of malignancy. The intensity is about 870 units for the lung cancer patient, about 720 units for the heavy smoker, and about 320 units for the normal patient. That is, the heavy smoker has moved away from the domain of normalcy and is pathologically closer to the lung cancer patient. In short, the damage done to the lungs by heavy smoking can be quantified.

Also, it is noted that the band at 325 nm due to elastin and collagen is exclusively present for the sputum of the lung cancer patient and the heavy smoker. This means that we can detect lung cancer at a very early stage, taking collagen and elastin as specific sputum biomarkers of lung cancer.

It is further noted that the band at 325 nm is distinctly present in tumor tissue, blood plasma, and also in the sputum of the lung cancer patient only. It is significantly elevated in heavy smokers, and absent in normal persons.

Example 10

Figure 14:
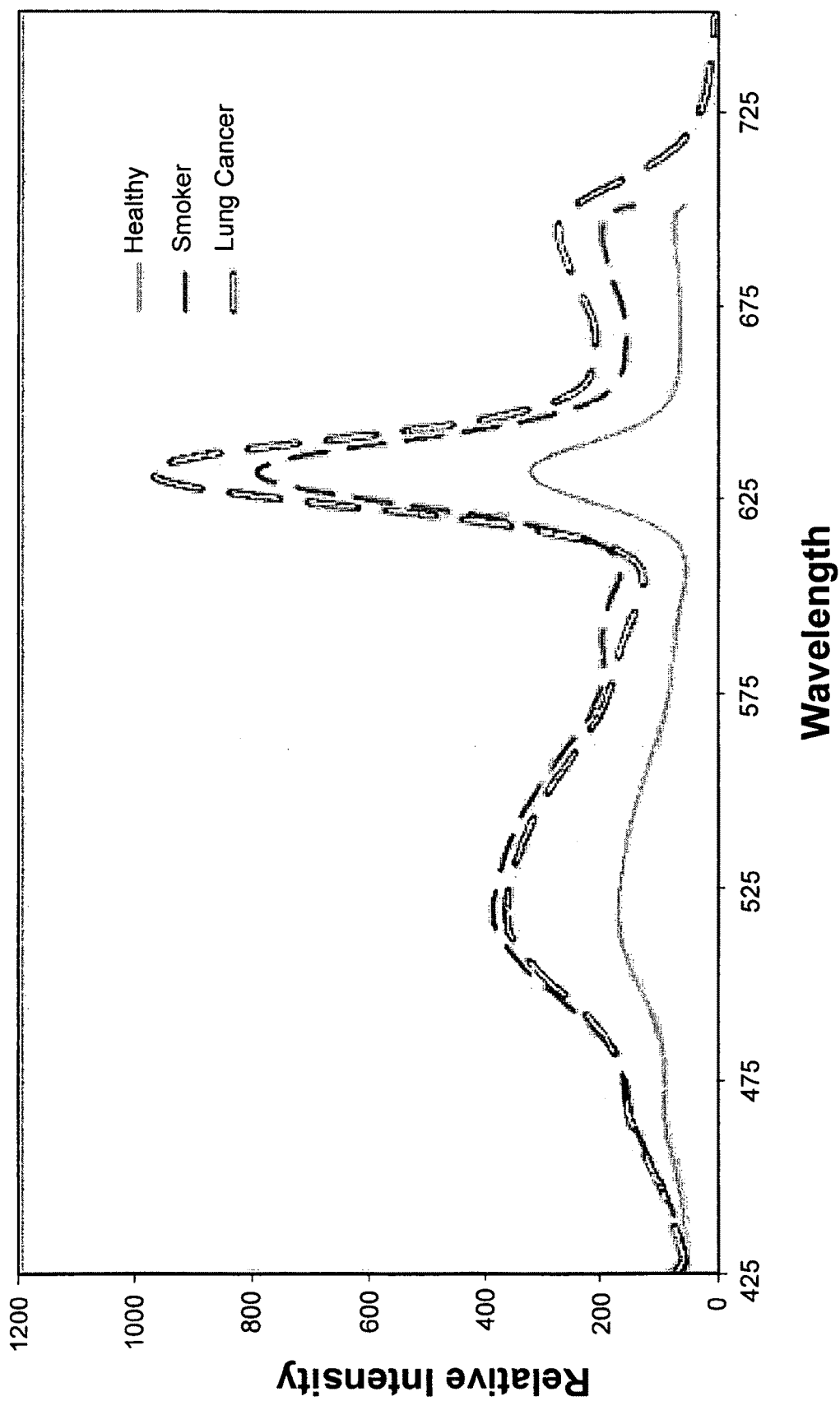
FIG. 14 shows the fluorescence emission spectra at an excitation wavelength of 400 nm of sputum samples of the same set of persons as in FIG. 13.

FIG. 14 shows the fluorescence emission spectra (excitation at 400 nm) of sputum of the same set of persons as in Example 8. The similarity between the spectra of the lung cancer patient and the heavy smoker is quite obvious. Both have a similar shape, but in the cancer patient, porphyrin (630 nm) is very well elevated in comparison to the smoker, which, in turn, is elevated in comparison to healthy persons.

Example 11

Figure 15:
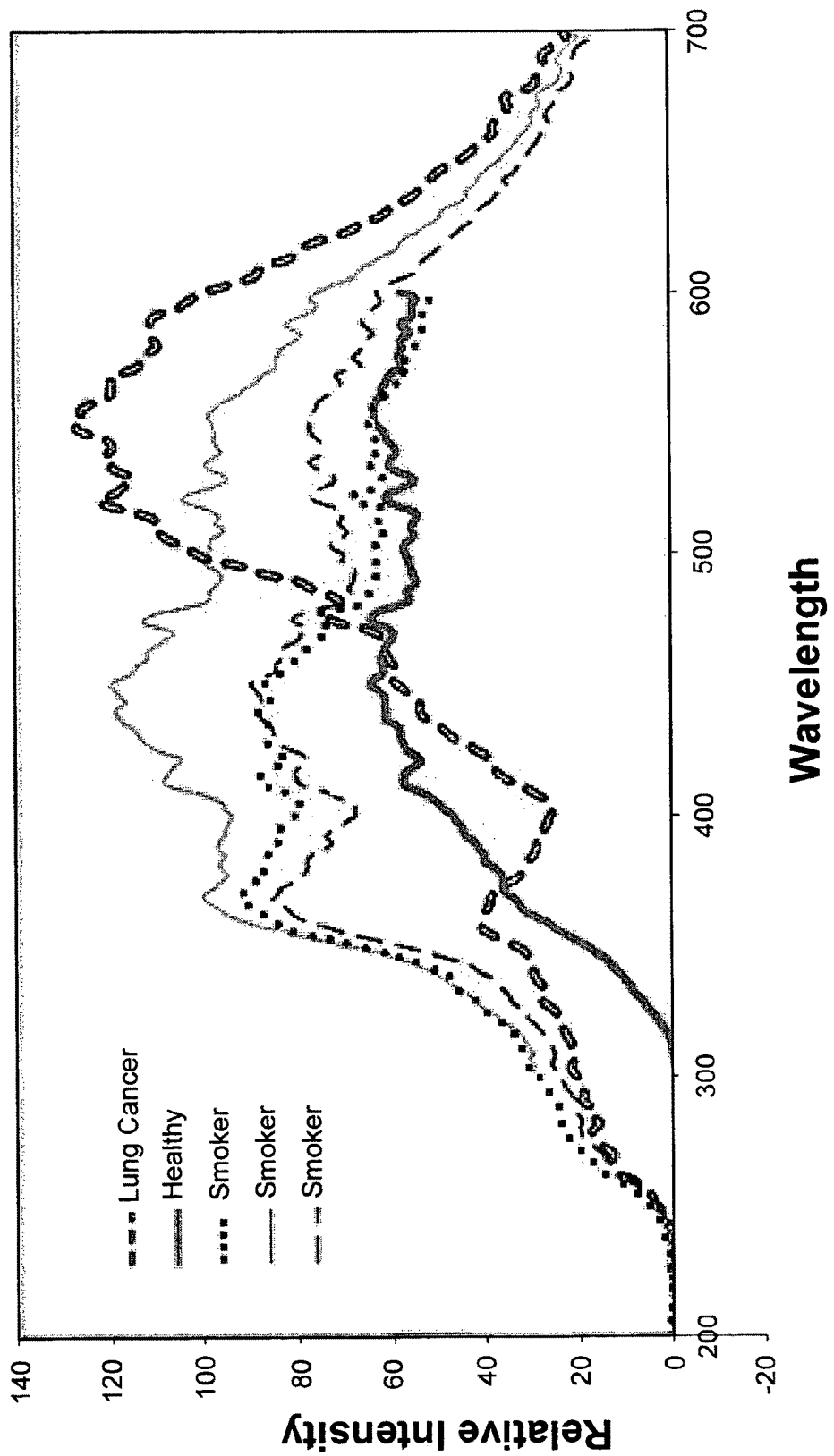
FIG. 15 shows the synchronous spectra with an offset of 10 nm of the urine samples of five persons: (a) a healthy person, (b) a lung cancer patient, and (c), (d) and (e) are 3 heavy smokers.

FIG. 15 shows the SS with a 10 nm offset of urine samples of (a) a healthy person; (b) a lung cancer patient; and (c), (d), and (e) three heavy smokers. The intensity at 350 nm, due to tryptophan, is about two times higher for the lung cancer patient and the heavy smokers than the for the normal person, indicative of cellular damage that has been done due to excessive smoking. It should be noted that for lung cancer patients, the intensity at 525 nm is abnormally high compared to all non-cancer sets (i.e., non-smokers and smokers).

Example 12

Figure 16:
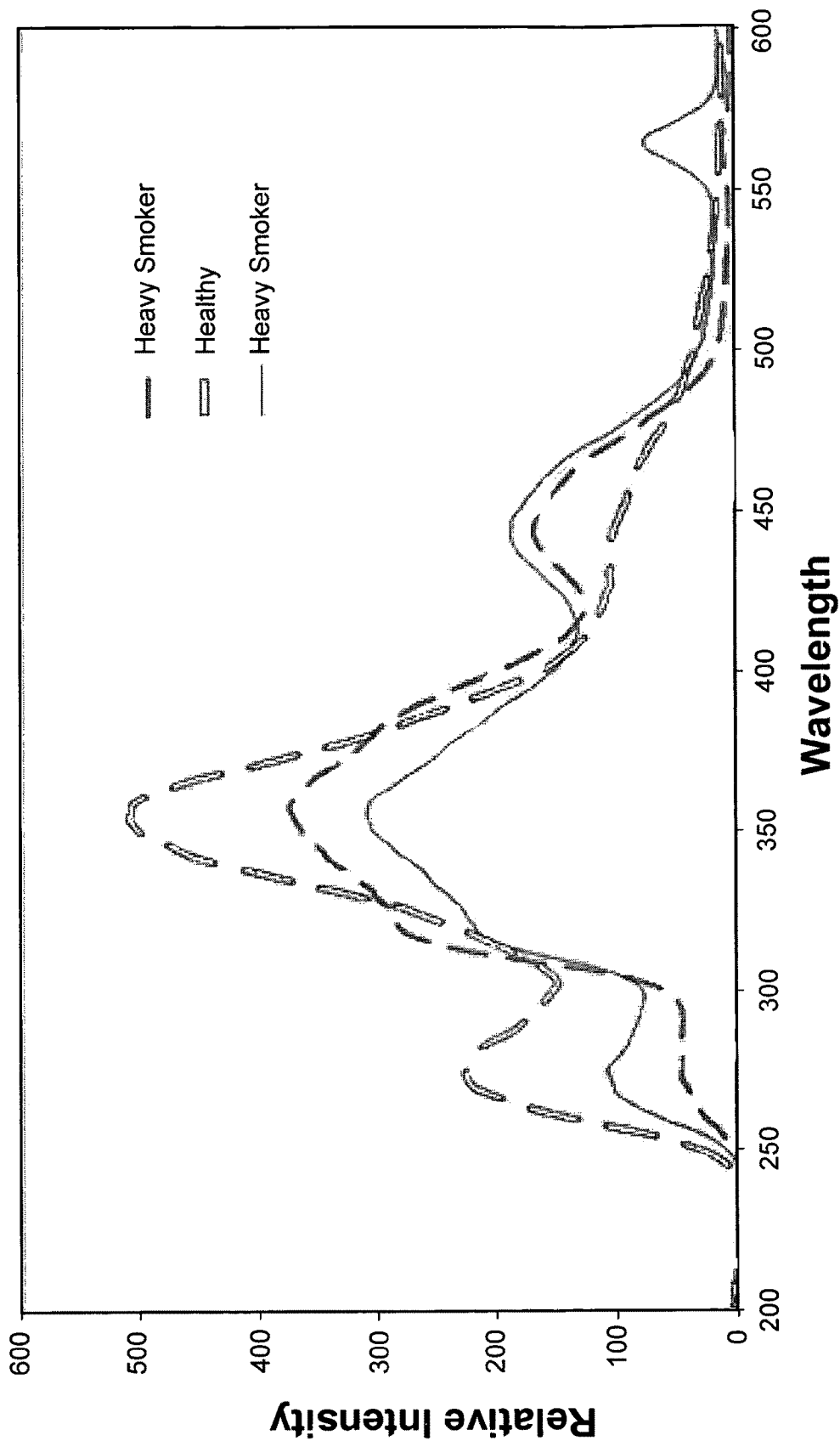
FIG. 16 shows the spectra of acetone extracts of the sputum of one healthy person and two heavy smokers.

FIG. 16 shows spectra from the acetone extract of the sputum of a healthy person and two heavy smokers. All three spectra show bands corresponding to tryptophan (280 nm), NADPH (360 nm) and flavin (450 nm). But for the healthy person, the band at 327 nm due to elastin is totally absent. For the two heavy smokers, it is distinctly present, indicative of cellular damage. It is important to note that the 450 nm peak is also elevated for the two heavy smokers, which is again an indication of abnormal metabolic activity. Between the two heavy smokers, the one with a band at 565 nm is at a greater risk because porphyrin is also elevated in the sputum.

Figure 18:
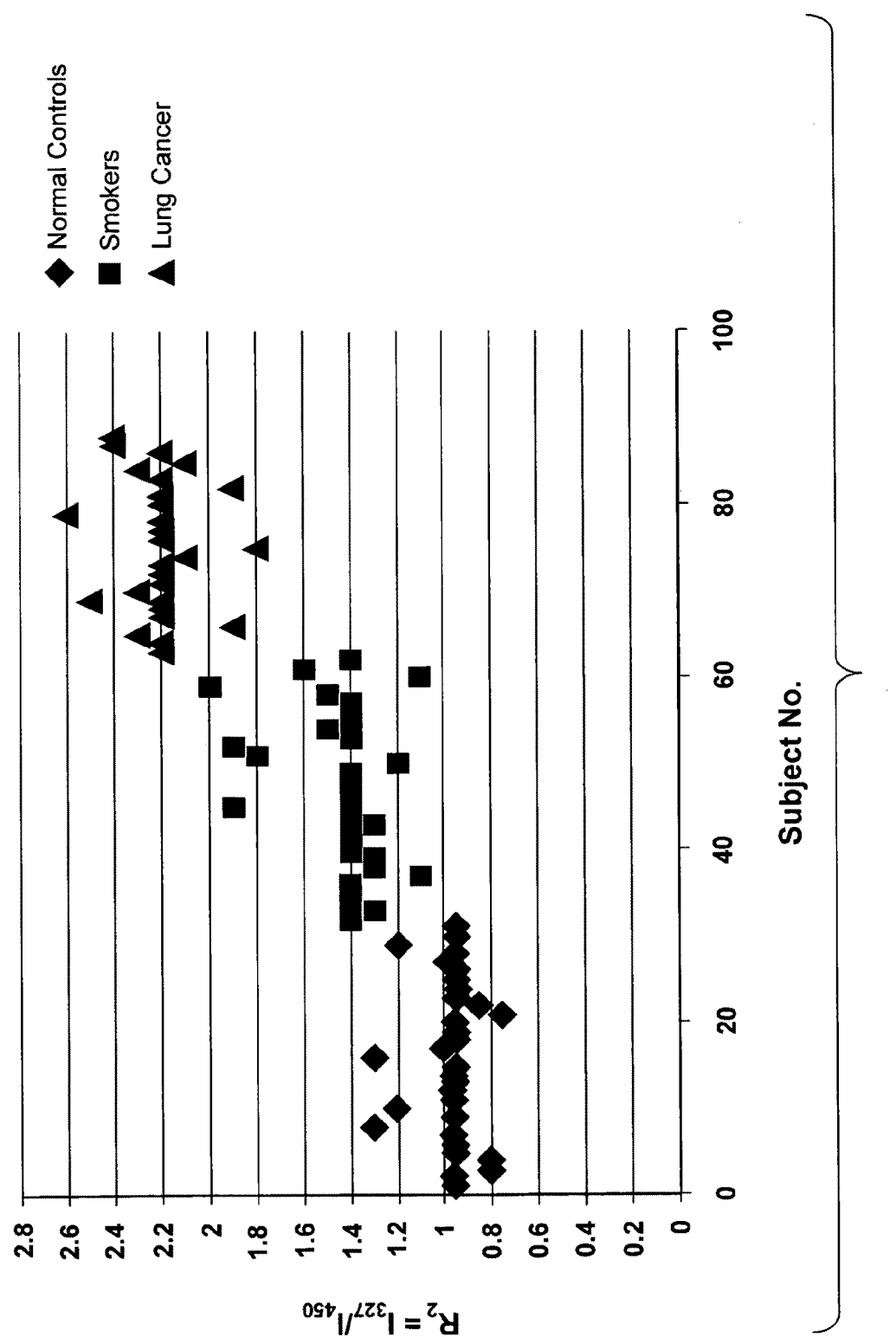
FIG. 18 shows the scatter plot of the ratio between $I_{327}/I_{450}$ in the synchronous spectra (SS) of acetone extracts of plasma of healthy persons, smokers, and lung cancer patients.

FIG. 18 shows a ratio parameter plot based on relative intensity between the bands at 327 nm and 450 nm in the acetone extract of blood plasma of healthy persons, smokers and lung cancer patients. FIG. 18 is presented as a scatter plot for the above three sets, each 31 in number. It should be noted that, for lung cancer patients, this ratio is about 220% greater than the healthy persons, and is 40% greater for the smokers than for the healthy persons. Here again, a few of the representative samples of the heavy smoker set are entering into the domain of lung cancer patients. From this point of view, this ratio may be used as a smoker's cancer risk index (SCRI).

All of these examples indicate that this new technique is capable of detecting pre-malignant and malignant conditions of lung cancer, and also stagewise monitoring of damage done to the lungs by heavy smoking and their asymptotic approach towards lung cancer.

It is to be understood that the present invention is not limited to the embodiments described above, but encompasses any and all embodiments within the scope of the following claims.

We claim:

1. A method for detecting lung cancer, comprising the steps of:
    irradiating a sample of a body fluid from a patient with light from an optical source at a wavelength of about 400 nm;
    detecting fluorescence from the sample over an emission band extending from about 425 nm to 700 nm;
    identifying and measuring fluorescence intensity maxima in the emission band corresponding to species of porphyrin, flavins, bile components, and background sample media;
    comparing relative concentrations of the species of porphyrin, flavins, bile components, and background sample media from the fluorescence intensities in order to diagnose cancer condition in the patient from whom the sample is taken;
    examining the same sample of body fluid to obtain synchronous fluorescence excitation and emission spectra with an offset between about 10 nm and 70 nm when the patient is diagnosed as cancerous according to the relative concentrations of the species of porphyrin, flavins, bile components, and background sample media; and
    diagnosing the patient as suffering from lung cancer when the synchronous spectra shows an excitation peak between about 325 nm and 330 nm due to the presence of elastin and collagen.

2. The method for detecting lung cancer according to claim 1, wherein the body fluid is selected from the group consisting of formed elements of the blood, blood plasma, urine, and sputum.

3. The method for detecting lung cancer according to claim 1, wherein the step of diagnosing the patient as suffering from lung cancer further comprises diagnosing the patient as suffering from lung cancer when the synchronous spectra shows an excitation peak at about 327 nm, corresponding to elevated levels of elastin and collagen.

4. The method for detecting lung cancer according to claim 1, wherein said step of irradiating the body fluid comprises irradiating an extract of formed elements from blood, the method further comprising the steps of:
   withdrawing a sample of blood from the subject;
   separating plasma from the formed elements of blood in the sample of blood;
   decanting the plasma to leave a residue of blood components; and
   extracting the residue of blood components with an extraction solvent to form the extract of formed elements from blood.

5. The method for detecting lung cancer according to claim 4, wherein said step of identifying and measuring fluorescence intensity maxima further comprises:
   measuring the fluorescence intensity at about 460 nm, corresponding to Raman scattering from the extraction solvent;
   measuring the fluorescence intensity at about 505 nm, corresponding to flavins and bile components;
   measuring the fluorescence intensity at about 585 nm, corresponding to anionic species of porphyrin;
   measuring the fluorescence intensity at about 630 nm, corresponding to neutral species of porphyrin; and
   measuring the fluorescence intensity at about 695 nm, corresponding to cationic species of porphyrin.

6. The method for detecting lung cancer according to claim 5, wherein said step of comparing relative concentrations further comprises the step of computing a ratio of the fluorescence intensity of the neutral species of porphyrin to the fluorescence intensity of the anionic species of porphyrin.

7. The method for detecting lung cancer according to claim 6, further comprising the step of tentatively diagnosing the subject as:
   free of cancer when the ratio is less than 1.5;
   at high risk for cancer when the ratio is greater than 1.5 and less than 2.25;
   in the early stages of cancer when the ratio is greater than 2.25 and less than 3; and
   in the advanced stages of cancer when the ratio is greater than 3.

8. The method for detecting lung cancer according to claim 6, further comprising the step of planning a course of further diagnostic testing and treatment according to the tentative diagnosis.

9. The method for detecting lung cancer according to claim 5, wherein said step of comparing relative concentrations further comprises the step of computing a ratio of the fluorescence intensity of the cationic species of porphyrin to the fluorescence intensity of the anionic species of porphyrin.

10. The method for detecting lung cancer according to claim 5, wherein said step of comparing relative concentrations further comprises the step of computing a ratio of the fluorescence intensity of the neutral species of porphyrin to the fluorescence intensity of the flavins and bile components.

11. The method for detecting lung cancer according to claim 5, wherein said step of comparing relative concentrations further comprises the step of computing a ratio of the fluorescence intensity of the anionic species of porphyrin to the fluorescence intensity of the background sample media.

12. The method for detecting lung cancer according to claim 5, wherein said step of comparing relative concentrations further comprises the step of computing a ratio of the fluorescence intensity of the flavins and bile components to the fluorescence intensity of the background sample media.

13. The method for detecting lung cancer according to claim 1, wherein said step of irradiating the body fluid comprises irradiating a sample of an extract from urine, the urine being extracted with an extraction solvent.

14. The method for detecting lung cancer according to claim 13, wherein said step of comparing relative concentrations further comprises the steps of:
   measuring the fluorescence intensity at about 470 nm;
   measuring the fluorescence intensity at about 520 nm;
   measuring the fluorescence intensity at about 550 nm; and
   measuring the fluorescence intensity at about 620 nm.

15. The method for detecting lung cancer according to claim 14, wherein said step of comparing relative concentrations further comprises the step of computing a ratio of the fluorescence intensity at 520 nm to the fluorescence intensity at about 470 nm.

16. The method for detecting lung cancer according to claim 15, further comprising the step of tentatively diagnosing the subject as:
   free of cancer when the ratio is less than 1;
   at high risk for cancer when the ratio is greater than 1.2 and less than 1.4;
   in the early stages of cancer when the ratio is greater than 1.4 and less than 1.6; and
   in the advanced stages of cancer when the ratio is greater than 1.6.

17. The method for detecting lung cancer according to claim 1, further comprising the steps of
   examining the synchronous spectra for fluorescence intensity maxima in the emission band corresponding to tyrosine, tryptophan, NAD(P)H, elastin and collagen; and
   comparing relative concentrations of tryptophan, tyrosine, elastin, collagen and NAD(P)H to further diagnose lung cancer conditions in the patient from whom the sample is taken.

18. The method for detecting lung cancer according to claim 1, wherein the body fluid is sputum, the method further comprising the steps of:
   fixing a fluorescence detector to detect fluorescent emissions from a sample of a body fluid at a wavelength of about 340 nm;
   irradiating the sample with light from an optical source over an excitation band spectrum extending from about 200 nm to 320 nm;
   examining the spectrum for absorption peaks at about 280 nm corresponding to tryptophan and at about 260 nm corresponding to tyrosine;
   computing the ratio of intensity of absorption peaks for tryptophan to tyrosine when present;
   determining that the patient is healthy when the ratio is about 1:0.8;
   determining that the patient has cancer when the ratio is about 2:1; and
   determining that the patient is at risk for developing cancer when the ratio is between 1:1 and 2:1.

\* \* \* \* \*